(12) United States Patent
Iikubo et al.

(10) Patent No.: US 7,862,512 B2
(45) Date of Patent: Jan. 4, 2011

(54) BLOOD VESSEL ENDOTHELIUM FUNCTION EVALUATING APPARATUS PROVIDED WITH AN ELECTRONIC CONTROL DEVICE

(75) Inventors: Katsushi Iikubo, Nagoya (JP); Hidehito Sasaki, Nagoya (JP); Hidenori Suzuki, Nagoya (JP); Hiromasa Tsukahara, Nagoya (JP); Chikao Harada, Nagoya (JP); Hitoshi Hirano, Nagoya (JP); Hiroshi Masuda, Nagoya (JP)

(73) Assignee: Unex Corporation, Nagoya (JP)

( * ) Notice: Subject to any disclaimer, the term of this patent is extended or adjusted under 35 U.S.C. 154(b) by 0 days.

(21) Appl. No.: 11/507,564

(22) Filed: Aug. 22, 2006

(65) Prior Publication Data

US 2007/0055152 A1    Mar. 8, 2007

(30) Foreign Application Priority Data

Aug. 29, 2005    (JP)    ............................. 2005-247690

(51) Int. Cl.
*A61B 8/00* (2006.01)
(52) U.S. Cl. ..................................... 600/459; 600/445
(58) Field of Classification Search ................ 600/443, 600/444, 445, 459, 437; 9/437, 443, 444, 9/445, 459
See application file for complete search history.

(56) References Cited

U.S. PATENT DOCUMENTS

| | | | | |
|---|---|---|---|---|
| 3,470,868 A | * | 10/1969 | Krause et al. ............... | 600/445 |
| 4,282,879 A | * | 8/1981 | Kunii et al. .................. | 600/445 |
| 4,370,985 A | * | 2/1983 | Takeichi et al. ............. | 600/440 |
| 4,381,787 A | * | 5/1983 | Hottinger .................... | 600/443 |
| 4,390,025 A | * | 6/1983 | Takemura et al. ........... | 600/440 |
| 4,399,822 A | * | 8/1983 | Theumer .................... | 600/445 |
| 4,444,197 A | * | 4/1984 | Koyano et al. .............. | 600/443 |
| 4,721,113 A | * | 1/1988 | Stewart et al. .............. | 600/449 |
| 5,170,790 A | * | 12/1992 | Lacoste et al. .............. | 600/437 |
| 5,572,999 A | * | 11/1996 | Funda et al. ................ | 600/118 |
| 5,769,079 A | * | 6/1998 | Hossack ...................... | 600/454 |
| 5,932,807 A | * | 8/1999 | Mallart ........................ | 73/641 |
| 5,944,666 A | * | 8/1999 | Hossack et al. ............. | 600/458 |
| 6,423,002 B1 | * | 7/2002 | Hossack ...................... | 600/439 |
| 6,554,759 B2 | * | 4/2003 | Fontayne et al. ............ | 600/7 |

(Continued)

FOREIGN PATENT DOCUMENTS

JP    A 2003-245280    9/2003

*Primary Examiner*—Brian Casler
*Assistant Examiner*—Peter Luong
(74) *Attorney, Agent, or Firm*—Oliff & Berridge, PLC

(57) ABSTRACT

An apparatus for measuring a short-axis image of a blood vessel under a skin of a living being, the apparatus including an ultrasonic probe including an ultrasonic array which has a plurality of ultrasonic transducers arranged in one direction in an emission surface and which emits, from the emission surface, an ultrasonic beam toward the blood vessel, the ultrasonic probe additionally including a main frame which is adapted to be placed on the skin of the living being, an x-axis supporting device which is supported by the main frame and which supports the ultrasonic array such that the ultrasonic array is rotatable about an x axis parallel to the direction of arrangement of the ultrasonic transducers in the emission surface, and an x-axis control device which controls a posture of the ultrasonic array supported by the x-axis supporting device such that in a y-z plane, the emission surface of the ultrasonic array is parallel to the blood vessel.

8 Claims, 18 Drawing Sheets

U.S. PATENT DOCUMENTS

| | | |
|---|---|---|
| 6,623,431 B1 * | 9/2003 | Sakuma et al. .............. 600/443 |
| 2001/0021809 A1 * | 9/2001 | De Jong et al. ............. 600/458 |
| 2001/0039379 A1 * | 11/2001 | Hagelauer ................... 600/437 |
| 2002/0049381 A1 * | 4/2002 | Eck et al. .................... 600/447 |
| 2004/0015080 A1 * | 1/2004 | Kelly et al. ................. 600/437 |
| 2004/0122324 A1 * | 6/2004 | Zan ............................ 600/459 |
| 2004/0267135 A1 * | 12/2004 | Takeuchi .................... 600/459 |
| 2005/0020917 A1 * | 1/2005 | Scherch ..................... 600/437 |
| 2005/0085730 A1 * | 4/2005 | Flesch et al. ................ 600/459 |
| 2005/0187473 A1 * | 8/2005 | Boctor et al. ............... 600/437 |
| 2006/0184033 A1 * | 8/2006 | Cerofolini .................. 600/459 |
| 2007/0016058 A1 * | 1/2007 | Kerwin ...................... 600/459 |

* cited by examiner

ROTATION ABOUT X AXIS

ROTATION ABOUT Y AXIS

BLOOD VESSEL ENDOTHELIUM FUNCTION EVALUATING APPARATUS PROVIDED WITH AN ELECTRONIC CONTROL DEVICE

The present application is based on Japanese Patent Application No. 2005-247690 filed on Aug. 29, 2005, the contents of which are incorporated herein by reference.

BACKGROUND OF THE INVENTION

1. Field of the Invention

The present invention relates to a blood-vessel-image measuring apparatus that measures, with an ultrasonic probe including an ultrasonic array that emits, from an emission surface thereof, an ultrasonic beam, an image including a blood vessel that underlies a skin of a living being and has an endothelium.

2. Related Art Statement

There has been proposed a blood-vessel-image measuring apparatus that measures, with an ultrasonic array that is lightly contacted with a skin of a living being (e.g., a living person) via a coupling agent such as a jelly and emits an ultrasonic beam toward the skin, an image including a blood vessel underlying the skin. This measuring apparatus is disclosed by, e.g., Japanese Patent Application Publication No. 2003-245280. In the measuring apparatus disclosed by this document, an ultrasonic probe supported by a free end of a robot arm is lightly pressed on a portion of the person to be inspected, so as to obtain a transverse cross-section image (i.e., a short-axis image) of the blood vessel under the skin and/or a longitudinal cross-section image (i.e., a long-axis image) of the blood vessel.

SUMMARY OF THE INVENTION

The above-indicated blood-vessel-image measuring apparatus is used to measure the changes of diameter of blood vessel of a living being and thereby evaluate the function or condition of endothelium of the blood vessel. However, since the accuracy of measurement of the blood-vessel diameter has limits, the accuracy of evaluation of the function of blood-vessel endothelium has not been sufficiently high.

It is therefore an object of the present invention to provide a blood-vessel-image measuring apparatus that can obtain a highly accurate diameter of a blood vessel.

The above object has been achieved by the present invention. According to a first mode of the present invention, there is provided an apparatus for measuring a short-axis image of a blood vessel under a skin of a living being, the apparatus comprising an ultrasonic probe including an ultrasonic array which has a plurality of ultrasonic transducers arranged in one direction in an emission surface and which emits, from the emission surface, an ultrasonic beam toward the blood vessel, the ultrasonic probe additionally including a main frame which is adapted to be placed on the skin of the living being, an x-axis supporting device which is supported by the main frame and which supports the ultrasonic array such that the ultrasonic array is rotatable about an x axis parallel to the direction of arrangement of the ultrasonic transducers in the emission surface, and an x-axis control device which controls a posture of the ultrasonic array supported by the x-axis supporting device such that in a y-z plane, the emission surface of the ultrasonic array is parallel to the blood vessel.

In the blood-vessel-image measuring apparatus according to the first mode of the present invention, the ultrasonic probe includes the main frame adapted to be placed on the skin of the living being, and the x-axis supporting device that is supported by the main frame and that supports the ultrasonic array such that the ultrasonic array is rotatable about the x axis parallel to the direction of arrangement of the ultrasonic transducers, and the x-axis control means or device controls the posture of the ultrasonic array supported by the x-axis supporting device such that in the y-z plane, the emission surface of the ultrasonic array extends parallel to the blood vessel. Therefore, in the state in which the emission surface from which the ultrasonic beam is emitted is parallel to the blood vessel, the reflection wave from the blood vessel can be obtained, and accordingly a highly clear and accurate transverse cross-section image of the blood vessel can be obtained.

According to a second mode of the present invention, there is provided an apparatus for measuring a short-axis image of a blood vessel under a skin of a living being, the apparatus comprising an ultrasonic probe including two ultrasonic arrays each of which has a plurality of ultrasonic transducers arranged in one direction in an emission surface and which emits, from the emission surface, an ultrasonic beam toward the blood vessel, the ultrasonic probe additionally including a main frame which is adapted to be placed on the skin of the living being, an x-axis supporting device which is supported by the main frame and which supports the two ultrasonic arrays such that the ultrasonic arrays are rotatable about an x axis parallel to the respective directions of arrangement of the ultrasonic transducers in the respective emission surfaces of the two ultrasonic arrays, an image displaying device which displays, in respective cross-section images obtained by the two ultrasonic arrays, respective positions of the blood vessel in a z-axis direction perpendicular to the respective emission surfaces of the two ultrasonic arrays, and an indication indicating a rotation direction about the x axis to decrease a difference of the respective positions of the blood vessel, and an input device which is manually operable to adjust a rotation of the two ultrasonic arrays, supported by the x-axis supporting device, about the x axis.

In the blood-vessel-image measuring apparatus according to the second mode of the present invention, the ultrasonic probe includes the main frame adapted to be placed on the skin of the living being, and the x-axis supporting device that is supported by the main frame and that supports the two ultrasonic arrays such that the ultrasonic arrays are rotatable about the x axis parallel to the respective directions of arrangement of the ultrasonic transducers; the image displaying device displays, in the respective cross-section images obtained by the two ultrasonic arrays, the respective positions of the blood vessel in the z-axis direction perpendicular to the respective emission surfaces of the two ultrasonic arrays, and the indication indicating the rotation direction about the x axis to decrease the difference of the respective positions of the blood vessel; and the input device is manually operable to adjust the rotation of the two ultrasonic arrays, supported by the x-axis supporting device, about the x axis. Thus, the input device is operated by an operator in the direction displayed by the image displaying device so as to change the rotation position of the ultrasonic arrays about the x axis and thereby zero the difference of the respective positions of the blood vessel. Thus, in the state in which the emission surfaces from which the ultrasonic beams are emitted are parallel to the blood vessel, the reflection waves from the blood vessel can be obtained, and accordingly highly clear and accurate transverse cross-section images of the blood vessel can be obtained.

According to a third mode of the present invention, there is provided an apparatus for measuring a short-axis image of a blood vessel under a skin of a living being, the apparatus comprising an ultrasonic probe including an ultrasonic array which has a plurality of ultrasonic transducers arranged in one direction in an emission surface and which emits, from the emission surface, an ultrasonic beam toward the blood vessel, the ultrasonic probe additionally including a main frame which is adapted to be placed on the skin of the living being, a z-axis supporting device which is supported by the main frame and which supports the ultrasonic array such that the ultrasonic array is rotatable about a z axis perpendicular to the emission surface, and a z-axis control device which controls a posture of the ultrasonic array supported by the z-axis supporting device such that in an x-y plane, a lengthwise direction of the ultrasonic array is perpendicular to the blood vessel.

In the blood-vessel-image measuring apparatus according to the third mode of the present invention, the ultrasonic probe includes the main frame adapted to be placed on the skin of the living being, and the z-axis supporting device that is supported by the main frame and that supports the ultrasonic array such that the ultrasonic array is rotatable about the z axis perpendicular to the emission surface, and the z-axis control means or device controls the posture of the ultrasonic array supported by the z-axis supporting device such that in the x-y plane, the lengthwise direction of the ultrasonic array is perpendicular to the blood vessel. Thus, in the state in which the lengthwise direction of the ultrasonic array is perpendicular to the blood vessel, the reflection wave from the blood vessel can be obtained, and accordingly a highly clear and accurate transverse cross-section image of the blood vessel can be obtained.

According to a fourth mode of the present invention, there is provided an apparatus for measuring a short-axis image of a blood vessel under a skin of a living being, the apparatus comprising an ultrasonic probe including two ultrasonic arrays each of which has a plurality of ultrasonic transducers arranged in one direction in an emission surface and which emits, from the emission surface, an ultrasonic beam toward the blood vessel, the ultrasonic probe additionally including a main frame which is adapted to be placed on the skin of the living being, a z-axis supporting device which is supported by the main frame and which supports the two ultrasonic arrays such that the ultrasonic arrays are rotatable about a z axis perpendicular to the respective emission surfaces of the two ultrasonic arrays, an image displaying device which displays, in respective cross-section images obtained by the two ultrasonic arrays, respective positions of the blood vessel in an x-axis direction parallel to the respective directions of arrangement of the ultrasonic transducers in the respective emission surfaces of the two ultrasonic arrays, and an indication indicating a rotation direction about the z axis to decrease a difference of the respective positions of the blood vessel, and an input device which is manually operable to adjust a rotation of the two ultrasonic arrays, supported by the z-axis supporting device, about the z axis.

In the blood-vessel-image measuring apparatus according to the fourth mode of the present invention, the ultrasonic probe includes the main frame adapted to be placed on the skin of the living being, and the z-axis supporting device that is supported by the main frame and that supports the two ultrasonic arrays such that the ultrasonic arrays are rotatable about the z axis perpendicular to the respective emission surfaces of the two ultrasonic arrays; the image displaying device displays, in the respective cross-section images obtained by the two ultrasonic arrays, the respective positions of the blood vessel in the x-axis direction parallel to the respective directions of arrangement of the ultrasonic transducers, and the indication indicating the rotation direction about the z axis to decrease the difference of the respective positions of the blood vessel; and the input device is manually operable to adjust the rotation of the two ultrasonic arrays, supported by the z-axis supporting device, about the z axis. Thus, the input device is operated by an operator in the direction displayed by the image displaying device so as to change the rotation position of the ultrasonic arrays about the z axis and thereby zero the difference of the respective positions of the blood vessel. Thus, in the state in which the respective lengthwise directions of the two ultrasonic arrays are perpendicular to the blood vessel, the reflection waves from the blood vessel can be obtained, and accordingly highly clear and accurate transverse cross-section images of the blood vessel can be obtained.

According to a fifth mode of the present invention, there is provided an apparatus for measuring a long-axis image of a blood vessel under a skin of a living being, the apparatus comprising an ultrasonic probe including an ultrasonic array which has a plurality of ultrasonic transducers arranged in one direction in an emission surface and which emits, from the emission surface, an ultrasonic beam toward the blood vessel, the ultrasonic probe additionally including a main frame which is adapted to be placed on the skin of the living being, an x-axis supporting device which is supported by the main frame and which supports the ultrasonic array such that the ultrasonic array is translatable in an x-axis direction parallel to the direction of arrangement of the ultrasonic transducers in the emission surface, a z-axis supporting device which is supported by the main frame and which supports the ultrasonic array such that the ultrasonic array is rotatable about a z axis which is perpendicular to the emission surface and which passes through a portion of the ultrasonic array, and a y-z-axis control device which controls the x-axis supporting device such that the portion of the ultrasonic array through which the z axis passes is positioned right above the blood vessel, and subsequently controls the z-axis supporting device such that the direction of arrangement of the ultrasonic transducers is parallel to the blood vessel.

In the blood-vessel-image measuring apparatus according to the fifth mode of the present invention, the ultrasonic probe includes the main frame adapted to be placed on the skin of the living being, the x-axis supporting device that is supported by the main frame and that supports the ultrasonic array such that the ultrasonic array is translatable in the x-axis direction parallel to the direction of arrangement of the ultrasonic transducers, and the z-axis supporting device that is supported by the main frame and that supports the ultrasonic array such that the ultrasonic array is rotatable about the z axis that is perpendicular to the emission surface and passes through a portion of the ultrasonic array, and the y-z-axis control means or device controls the x-axis supporting device such that the portion of the ultrasonic array through which the z axis passes is positioned right above the blood vessel, and subsequently controls the z-axis supporting device such that the direction of arrangement of the ultrasonic transducers is parallel to the blood vessel. Thus, the portion of the ultrasonic array through which the z axis passes is positioned right above the blood vessel, and the direction of arrangement of the ultrasonic transducers is made parallel to the blood vessel and accordingly, based on the reflection wave from the blood vessel, a highly clear and accurate longitudinal cross-section image of the blood vessel can be obtained.

According to a sixth mode of the present invention, there is provided an apparatus for measuring a long-axis image of a blood vessel under a skin of a living being, the apparatus comprising an ultrasonic probe including two ultrasonic arrays each of which has a plurality of ultrasonic transducers arranged in one direction in an emission surface and which emits, from the emission surface, an ultrasonic beam toward the blood vessel, the ultrasonic probe additionally including a main frame which is adapted to be placed on the skin of the living being, an x-axis supporting device which is supported by the main frame and which supports the two ultrasonic arrays such that the ultrasonic arrays are translatable in an x-axis direction parallel to the respective directions of arrangement of the ultrasonic transducers in the respective emission surfaces of the two ultrasonic arrays, a z-axis supporting device which is supported by the main frame and which supports the two ultrasonic arrays such that the two ultrasonic arrays are rotatable about a z axis which is perpendicular to the respective emission surfaces thereof and which passes therethrough, and an image displaying device which displays, in respective cross-section images obtained by the two ultrasonic arrays, respective positions of the blood vessel in the x-axis direction, and an indication indicating a rotation direction about the z axis to decrease a difference of the respective positions of the blood vessel, and an input device which is manually operable to adjust a movement of the two ultrasonic arrays, supported by the x-axis supporting device, in the x-axis direction, and a rotation of the two ultrasonic arrays, supported by the z-axis supporting device, about the z axis.

In the blood-vessel-image measuring apparatus according to the sixth mode of the present invention, the ultrasonic probe includes the main frame adapted to be placed on the skin of the living being, the x-axis supporting device that is supported by the main frame and that supports the two ultrasonic arrays such that the ultrasonic arrays are translatable in the x-axis direction parallel to the respective directions of arrangement of the ultrasonic transducers, and the z-axis supporting device that is supported by the main frame and that supports the two ultrasonic arrays such that the ultrasonic arrays are rotatable about the z axis that is perpendicular to the respective emission surfaces thereof and passes therethrough; the image displaying device displays, in the respective cross-section images obtained by the two ultrasonic arrays, the respective positions of the blood vessel in the x-axis direction, and the indication indicating the rotation direction about the z axis to decrease the difference of the respective positions of the blood vessel; and the input device is manually operable by an operator to adjust the movement of the two ultrasonic arrays, supported by the x-axis supporting device, in the x-axis direction, and the rotation of the two ultrasonic arrays, supported by the z-axis supporting device, about the z axis. Thus, the input device is manually operated to change or adjust the movement position of the two ultrasonic arrays in the x-axis direction, and the rotation of the same about the z axis, such that a portion of one of the two ultrasonic arrays through which the z axis passes is positioned right above the blood vessel, and the direction of arrangement of the ultrasonic transducers of the one ultrasonic array is made parallel to the blood vessel. Accordingly, based on the reflection wave from the blood vessel, a highly clear and accurate longitudinal cross-section image of the blood vessel can be obtained.

According to a seventh mode of the present invention, there is provided an apparatus for measuring an image of a blood vessel, including an endothelium, under a skin of a living being, the apparatus comprising an ultrasonic probe including an ultrasonic array which has a plurality of ultrasonic transducers arranged in one direction in an emission surface and which emits, from the emission surface, an ultrasonic beam toward the blood vessel, the ultrasonic probe additionally including a main frame which is adapted to be placed on the skin of the living being, a y-axis supporting device which is supported by the main frame and which supports the ultrasonic array such that the ultrasonic array is rotatable about a y axis perpendicular to the direction of arrangement of the ultrasonic transducers in the emission surface, and an emission-surface-angle control device which changes a rotation posture of the ultrasonic array about the y axis such that an angle to delete a ghost image produced by multiple reflection in the measured image is formed between the emission surface and an outer surface of the skin that is opposed to the emission surface.

In the blood-vessel-image measuring apparatus according to the seventh mode of the present invention, the ultrasonic probe includes the main frame adapted to be placed on the skin of the living being, and the y-axis supporting device that is supported by the main frame and that supports the ultrasonic array such that the ultrasonic array is rotatable about the y axis perpendicular to the direction of arrangement of the ultrasonic transducers, and the emission-surface-angle control means or device changes the rotation posture of the ultrasonic array about the y axis such that an angle to delete the ghost image produced by the multiple reflection in the measured image is formed between the emission surface and the surface of the skin that is opposed to the emission surface. Therefore, the emission surface of the ultrasonic probe is inclined relative to the surface of the skin opposed to the emission surface so as to prevent the multiple reflection, and accordingly a highly clear and accurate transverse cross-section image of an endothelium (i.e., an inner layer) of the blood vessel can be obtained.

According to an eighth mode of the present invention, there is provided an apparatus for measuring an image of a blood vessel, including an endothelium, under a skin of a living being, the apparatus comprising an ultrasonic probe including an ultrasonic array which has a plurality of ultrasonic transducers arranged in one direction in an emission surface and which emits, from the emission surface, an ultrasonic beam toward the blood vessel, the ultrasonic probe additionally including a main frame which is adapted to be placed on the skin of the living being, a y-axis supporting device which is supported by the main frame and which supports the ultrasonic array such that the ultrasonic array is rotatable about a y axis perpendicular to the direction of arrangement of the ultrasonic transducers in the emission surface, an image displaying device which displays an image of the blood vessel, including the endothelium, obtained by the ultrasonic array, and an input device which is manually operable to adjust a rotation of the ultrasonic array, supported by the y-axis supporting device, about the y axis.

In the blood-vessel-image measuring apparatus according to the eighth mode of the present invention, the ultrasonic probe includes the main frame adapted to be placed on the skin of the living being, and the y-axis supporting device that is supported by the main frame and that supports the ultrasonic array such that the ultrasonic array is rotatable about the y axis perpendicular to the direction of arrangement of the ultrasonic transducers; the image displaying device displays the image of the blood vessel, including the endothelium, obtained by the ultrasonic array; and the input device is manually operable to adjust the rotation of the ultrasonic array, supported by the y-axis supporting device, about the y axis. Therefore, the input device is manually operated till the emission surface of the ultrasonic probe is so inclined relative to the surface of the skin opposed to the emission surface as to prevent the multiple reflection, or the ghost image of the endothelium produced by the multiple reflection, and accordingly a highly clear and accurate transverse cross-section image of the endothelium (i.e., the inner layer) of the blood vessel can be obtained.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
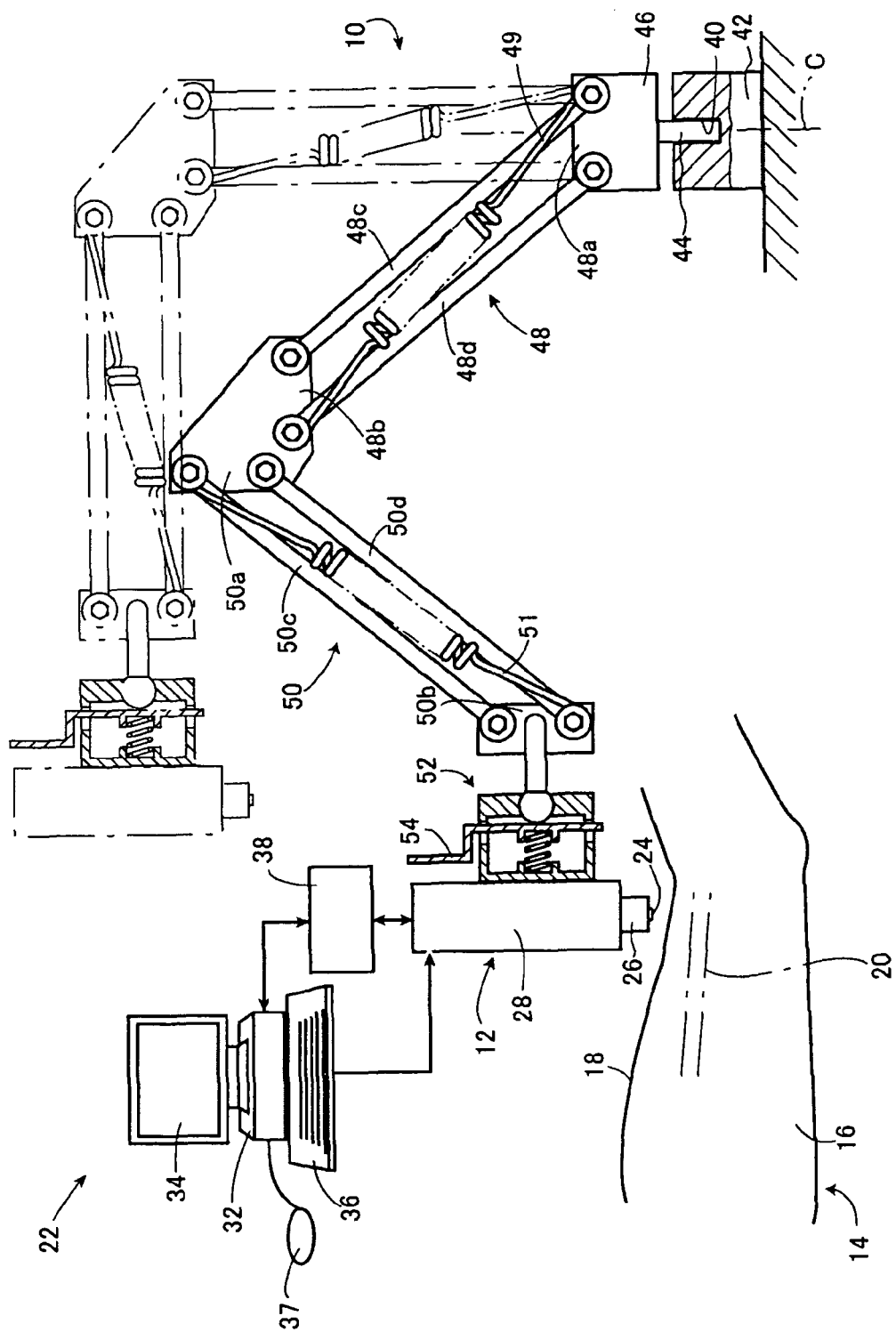
FIG. 1 is a schematic view of a general construction of a blood-vessel-image measuring apparatus as a first embodiment of the present invention.

Hereinafter, there will be described preferred embodiments of the present invention in detail by reference to the drawings. FIG. 1 is a front view for explaining a blood-vessel-image measuring apparatus 22 which includes an ultrasonic probe 12 as a sensor, and a sensor holding apparatus 10 that holds the ultrasonic probe 12, and which measures, using the ultrasonic probe 12 held on a surface of a skin 18 of an upper arm 16 of a living being 14 (e.g., a living person) as an object, a transverse-cross-section image (i.e., a short-axis image) and/or a longitudinal-cross-section image (i.e., a long-axis image) of a blood vessel (e.g., an artery) 20 located right below the skin 18.

Figure 2:
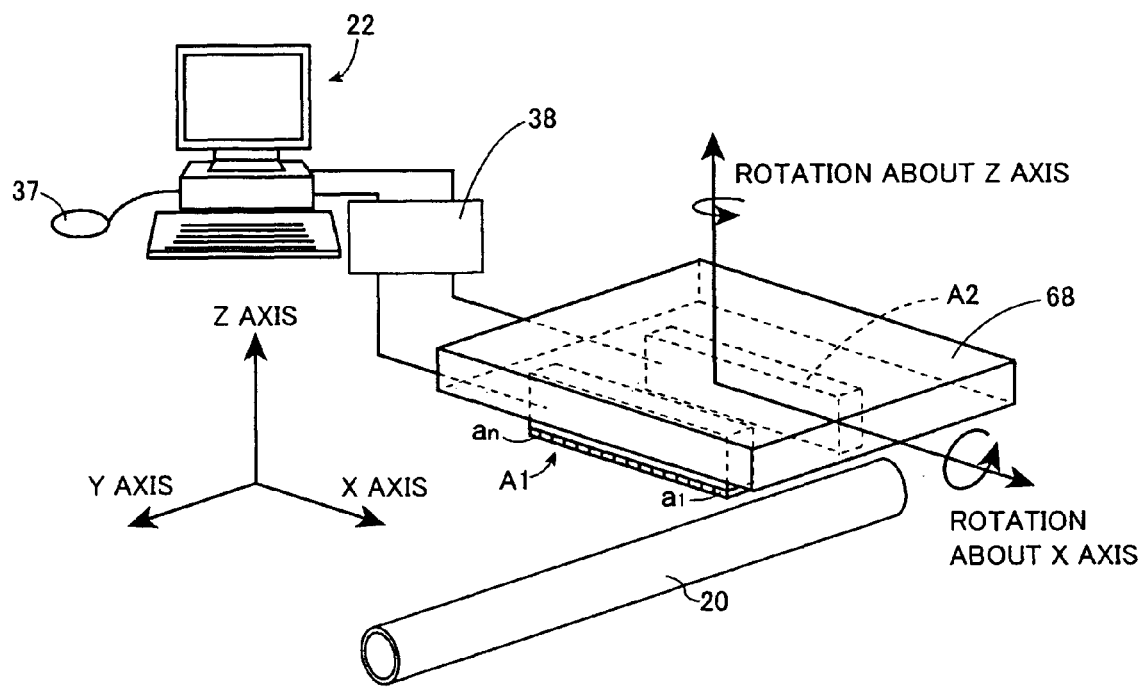
FIG. 2 is a view for explaining x, y, and z axes that are used to represent a posture, relative to a blood vessel, of two ultrasonic arrays provided in a free-end portion of an ultrasonic probe of the measuring apparatus of FIG. 1.

The ultrasonic probe 12 functions as a sensor that detects physical information of a living being, and has a free-end portion 24 including a large number of ultrasonic transducers each of which is constituted by, e.g., a piezoelectric ceramics and which are arranged in two parallel arrays, i.e., are provided in the form of two ultrasonic arrays A1, A2; a multiple-axis driving or positioning device 26; and a main frame 28 that supports the free-end portion 24 via the multiple-axis positioning device 26. Each of the two ultrasonic arrays A1, A2 includes ultrasonic transducers $a_1, a_2, \ldots, a_n$ (FIG. 2). FIG. 2 shows an xyz orthogonal system that is used in the present embodiment. The y axis indicates a longitudinal direction of the blood vessel 20; the x axis indicates a direction perpendicular to the blood vessel 20 on the surface of the skin 18; and the z axis indicates a direction perpendicular to the skin surface 18. As will be described later, the two ultrasonic arrays A1, A2 can be rotated by the multiple-axis positioning device 26 about each of the x axis and the z axis.

Figure 3:
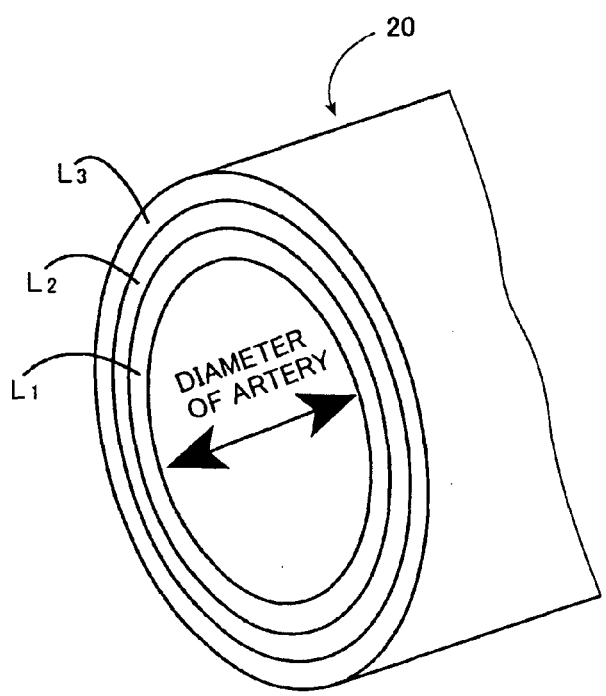
FIG. 3 is an enlarged view for explaining a multiple-layer structure of the blood vessel whose image is to be measured by the measuring apparatus of FIG. 1.

As shown in FIG. 3, the blood vessel 20 has a three-layer structure including an inner layer (i.e., tunica intima) $L_1$, an intermediate layer (tunica media) $L_2$, and an outer layer (tunica externa) $L_3$. When an image is taken using an ultrasonic wave, reflection from the intermediate layer $L_2$ is very weak and accordingly only the inner layer $L_1$ and the outer layer $L_3$ are displayed. In an actual image, an inner space of the blood vessel 20 and the intermediate layer $L_2$ thereof are displayed in black; the inner layer $L_1$ and the outer layer $L_3$ are displayed in white; and the tissue is displayed in white and black. The inner layer $L_1$ is so displayed as to have a thickness much smaller than that of the outer layer $L_3$. Thus, it is more difficult to display the inner layer $L_1$ than the outer layer $L_3$. However, when an evaluation is carried out using FMD (i.e., flow-mediated dilation), it is desirable to use a rate of change of a diameter of the inner layer $L_1$.

The blood-vessel-image measuring apparatus 22 further includes an electronic control device 32 that is constituted by a so-called microcomputer; a monitor-image displaying device 34; a keyboard 36 and a mouse 37 as an input device; and an ultrasonic-wave control circuit 38. The electronic control device 32 controls the ultrasonic-wave control circuit 38 to supply drive signals to the ultrasonic arrays A1, A2 at the free-end portion 24 of the ultrasonic probe 12, so that the ultrasonic arrays A1, A2 generate ultrasonic waves, receive the ultrasonic waves reflected from the tissue located under the skin surface 18, and produce reflected-ultrasonic-wave signals. The control device 32 receives the reflected-ultrasonic-wave signals from the ultrasonic arrays A1, A2, processes the thus received signals, produces ultrasonic images of the tissue under the skin surface 18, and controls the monitor-image displaying device 34 to display the thus produced ultrasonic images. More specifically described, when the control device 32 produces the transverse-cross-section images (i.e., the short-axis images) of the blood vessel 20, the control device 32 controls the three-axis positioning device 26 to position the ultrasonic arrays A1, A2 of the free-end portion 24 relative to the blood vessel 20 such that the ultrasonic arrays A1, A2 extend in a direction perpendicular to the blood vessel 20; and when the control device 32 produces the longitudinal-cross-section images (i.e., the long-axis images) of the blood vessel 20, the control device 32 controls the three-axis positioning device 26 to position the ultrasonic arrays A1, A2 relative to the blood vessel 20 such that the ultrasonic arrays A1, A2 extend in a direction parallel to the blood vessel 20.

The ultrasonic probe 12 is held by the sensor holding apparatus 10, such that the probe 12 takes a desirable posture and touches, at a desirable or predetermined position in a three-dimensional space, the skin surface 18 of the upper arm 16 of the living being 14 as the object, without changing a shape of the blood vessel 20 located right below the skin surface 18. Usually, a well-known coupling agent such as a jelly is interposed between the skin surface 18 and an outer surface of the free end portion 24 of the ultrasonic probe 12, for the purpose of preventing the attenuation of ultrasonic waves, and/or the reflection or scattering thereof at the interface of the two elements 18, 24, and thereby obtaining clear ultrasonic images. The jelly may be a gel of a hydrophilic polymer that contains water at a high rate and has an intrinsic impedance [=(sound speed)×(density)] sufficiently higher than that of air, and accordingly effectively restrains the attenuation of ultrasonic waves signals transmitted and received. The jelly is, e.g., agar, but it may be replaced with a water bag, i.e., a water packed in a resin-based bag; olive oil; or glycerin.

The sensor holding apparatus 10 is fixed in position to a support member such as a desk or a seat. More specifically described, the sensor holding apparatus 10 includes a base member 42 having a fitting hole 40 extending along a vertical axis line, C; and a rotatable member 46 that has a fitting axis portion 44 that fits in the fitting hole 40 such that the axis portion 44 is rotatable relative thereto, so that the rotatable member 46 is rotatable about the vertical axis line C relative to the base member 42. The sensor holding apparatus 10 additionally includes a first link device 48 that is constituted by four links 48a, 48b, 48c, 48d including a horizontal, first stationary link 48a fixed to (i.e., integral with) the rotatable member 46; a second link device 50 that is constituted by four links 50a, 50b, 50c, 50d including a vertical, second stationary link 50a fixed to (i.e., integral with) an end portion of the first link device 48; a universal joint 52 that is fixed to an end portion of the second link device 50, connects the ultrasonic probe 12 to the same 50, and supports the probe 12 such that the probe 12 is universally rotatable; and a stopper device 56 that includes an operable lever 54 and that fixes the universal joint 52 while the lever 54 is not operated by an operator, and releases the fixation of the joint 52, i.e., permits the universal rotation of the joint 52 while the lever 54 is operated by the operator.

The first link device 48 includes the first stationary link 48a; a first movable link 48b extending parallel to the first stationary link 48a; and a pair of first pivotable links 48c, 48d which extend parallel to each other and each of which is pivotably connected, at two opposite ends thereof, to the first stationary link 48a and the first movable link 48b, respectively, so that the first stationary link 48a, the first movable link 48b, and the two first pivotable links 48c, 48d cooperate with each other to define a parallelogram. The first stationary link 48a is fixed to the rotatable member 46 such that the first movable link 48b is movable in a plane containing the vertical axis line C. In association with the first link device 48, there is provided a first coil spring 49 functioning as a first elastic member that produces a thrust having a directional component resisting a load applied to the first movable link 48b. The first coil spring 49 is connected at one end thereof to a connection point where one-first-pivotable-link 48c and the first stationary link 48a are connected to each other, and is connected at the other end thereof to a connection point where the other first pivotable link 48d and the first movable link 48b are connected to each other, such that a moment produced by the first coil spring 49 in a direction to move the first movable link 48b upward, and a moment produced by the load applied to the first movable link 48b in a direction to move the same 48b downward are substantially cancelled by each other.

The second link device 50 includes a pair of second pivotable links 50c, 50d that extend parallel to each other; and the second stationary link 50a and a second movable link 50b which extend parallel to each other and each of which is pivotably connected, at two opposite ends thereof, to the two second pivotable links 50c, 50d, respectively, so that the second stationary link 50a, the second movable link 50b, and the two second pivotable links 50c, 50d cooperate with each other to define a parallelogram. The second stationary link 50a is fixed to the first movable link 48b such that the second stationary link 50a extends in a direction substantially perpendicular to the first stationary link 48a and such that the second movable link 50b is movable in the plane containing the vertical axis line C. In association with the second link device 50, there is provided a second coil spring 51 functioning as a second elastic member that produces a thrust having a directional component resisting a load applied to the second movable link 50b. The second coil spring 51 is connected at one end thereof to a connection point where one second pivotable link 50c and the second stationary link 50a are connected to each other, and is connected at the other end thereof to a connection point where the other second pivotable link 50d and the second movable link 50b are connected to each other, such that a moment produced by the second coil spring 51 in a direction to move the second movable link 50b upward, and a moment produced by the load applied to the second movable link 50b in a direction to move the same 50b downward are substantially cancelled by each other. Owing to the respective moment-canceling actions of the first and second coil springs 49, 51, the sensor holding apparatus 10 can hold the ultrasonic probe 12 such that the probe 12 is stopped at a desirable position, or is slowly moved downward, in the three-dimensional space, and such that the outer surface of the free end portion 24 of the probe 12 lightly touches the skin surface 18 without deforming the blood vessel 20 and closely contacts the same 18 via the coupling agent such as the jelly, as indicated by solid lines in FIG. 1. In addition, the ultrasonic probe 12 can be moved upward as indicated by one-dot chain lines in FIG. 1.

Figure 4:
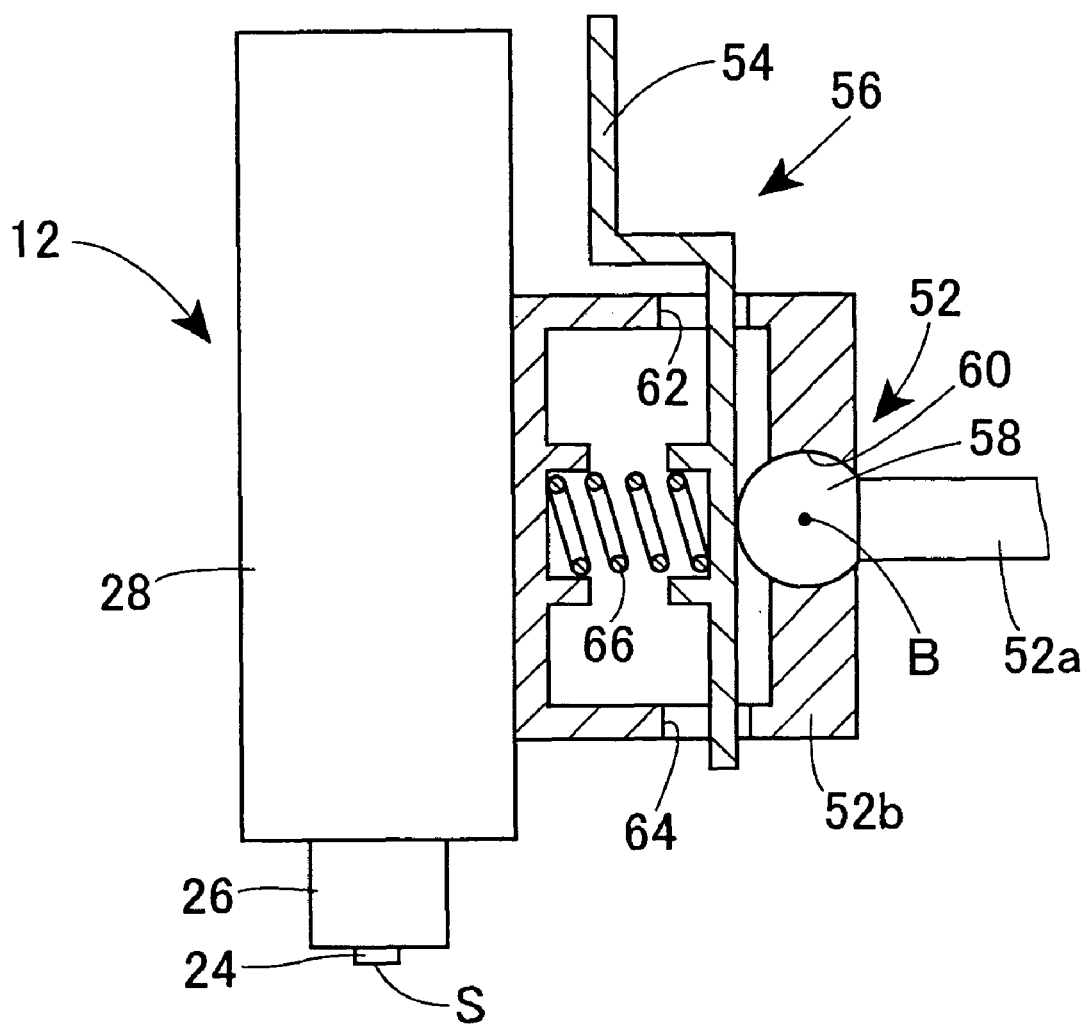
FIG. 4 is an enlarged view showing an end portion of a sensor holding apparatus of the measuring apparatus of FIG. 1, and the ultrasonic probe supported by the end portion.

FIG. 4 is an enlarged view of the universal joint 52 and the stopper device 56. As shown in the figure, the universal joint 52 includes a first connection member 52a having a base end portion fixed to the second movable link 50b, and a free end portion 58 having a spherical shape; and a second connection member 52b that has a fitting hole 60 in which the spherical end portion 58 of the first connection member 52a slideably fits, and that is connected to the spherical end portion 58 such that the second connection member 52b is universally rotatable about a center, B, of the spherical portion 58. The second connection member 52b has two guide holes 62, 64 that cooperate with each other to guide the operable lever 54 of the stopper device 56 such that the operable lever 54 is movable toward, and away from, the spherical end portion 58 of the first connection member 52a.

The stopper device 56 includes, in addition to the operable lever 54, a pressing spring 66 that presses the operable lever 54 against the spherical end portion 58 of the first connection member 52a. In a usual state in which the operable lever 54 is not in use, the pressing spring 66 presses the operable lever 54 against the spherical portion 58, so as to inhibit the rotation of the universal joint 52 and thereby fix the same 52. However, when the operable lever 54 is used or operated by the operator against the biasing force of the pressing spring 66, and is moved away from the spherical portion 58, the fixation of the universal joint 52 is released and the universal rotation of the same 52 is permitted. Thus, the ultrasonic probe 12 can take a desirable posture.

Figure 5:
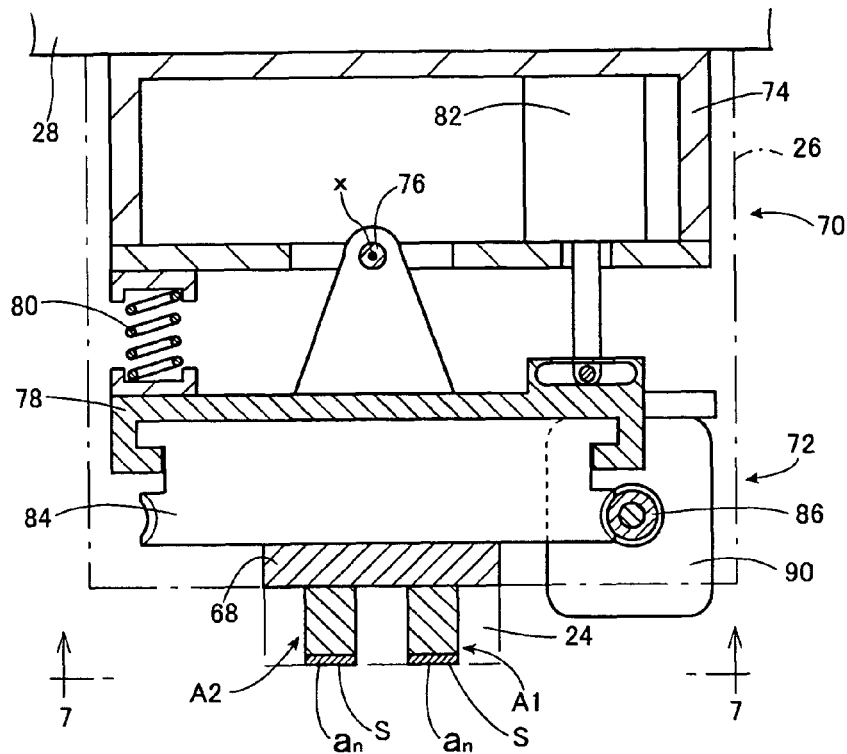
FIG. 5 is a cross-section view for explaining a multiple-axis driving or positioning device of the ultrasonic probe that includes an x-axis rotating device and a z-axis rotating device and positions the ultrasonic arrays relative to the blood vessel.
Figure 6:
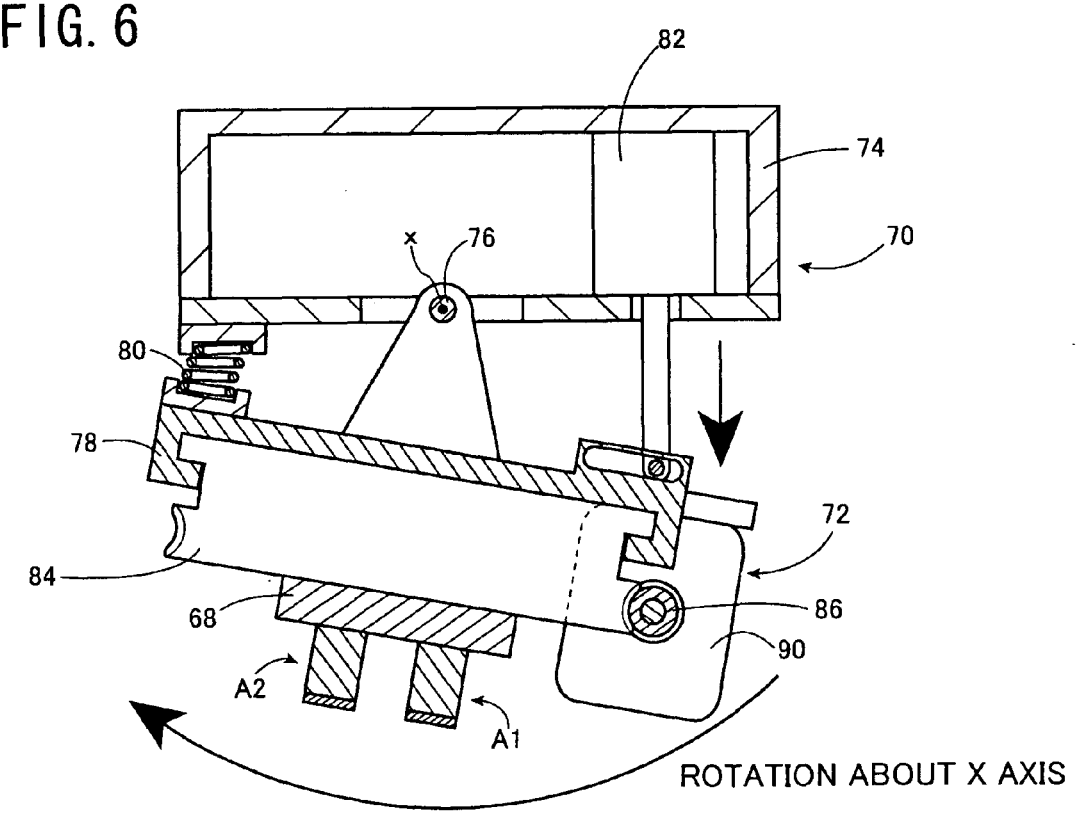
FIG. 6 is a cross-section view showing a state in which a rotation position of the ultrasonic arrays about the x axis has been changed by the x-axis rotating device.
Figure 7:
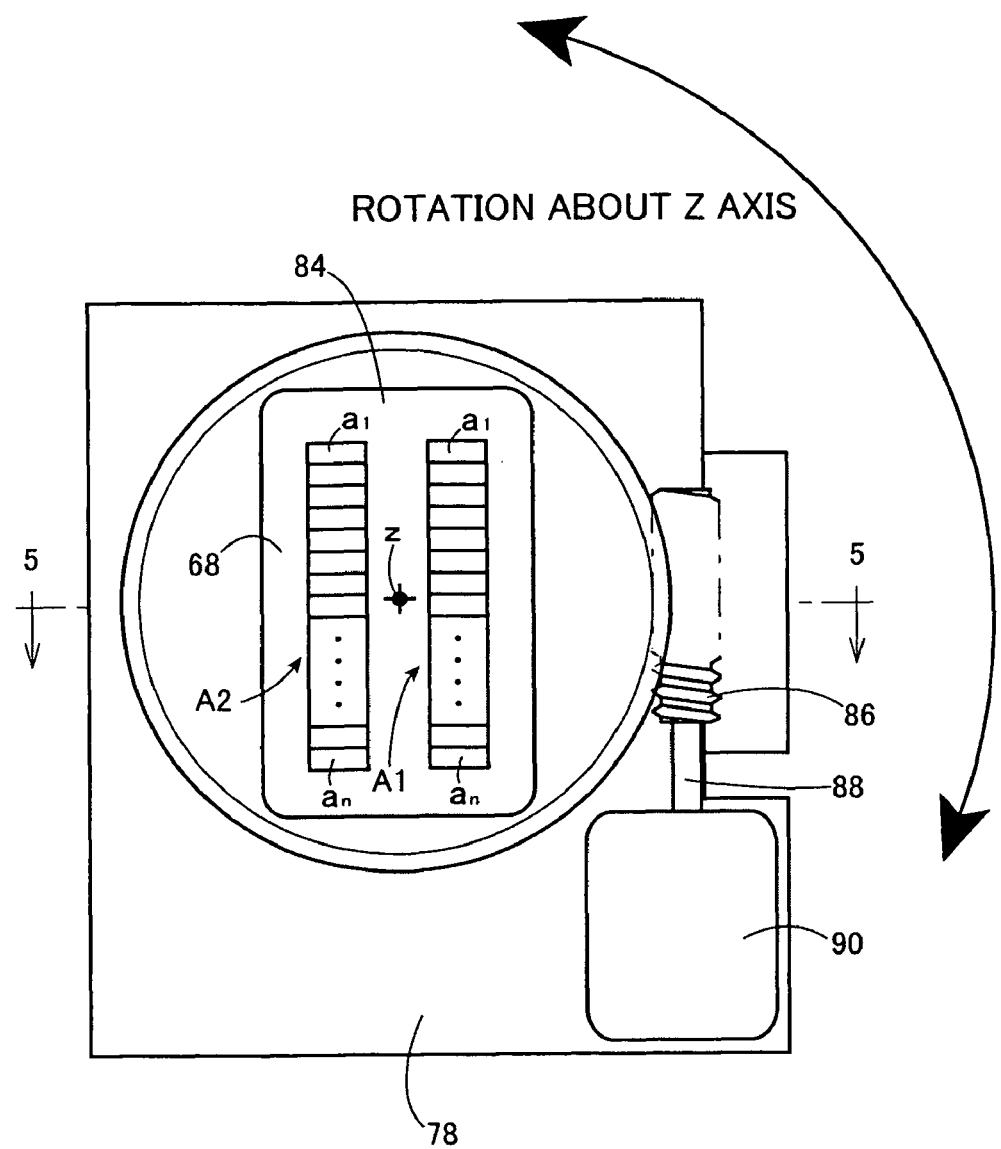
FIG. 7 is a cross-section view showing a state in which a rotation position of the ultrasonic arrays about the z axis has been changed by the z-axis rotating device.

As shown in FIG. 5, the two ultrasonic arrays A1, A2 that extend parallel to each other are fixed to a substrate 68 as a portion of the free-end portion 24 that is supported by the main frame 28 of the ultrasonic probe 12 via the multiple-axis positioning device 26. As shown in FIGS. 5, 6, and 7, the multiple-axis positioning device 26 includes an x-axis rotating device 70 that changes and selects a rotation position of the two ultrasonic arrays A1, A2 about the x axis; and a z-axis rotating device 72 that changes and selects a rotation position of the two ultrasonic arrays A1, A2 about the z axis. The x-axis rotating device 70 functions as an x-axis supporting device that supports the two ultrasonic arrays A1, A2 such that the two ultrasonic arrays A1, A2 are rotatable about the x axis; and the z-axis rotating device 72 functions as a z-axis supporting device that supports the two ultrasonic arrays A1, A2 such that the two ultrasonic arrays A1, A2 are rotatable about the z axis. The x-axis rotating device 70 includes a stationary frame 74 fixed to a lower end of the main frame 28; a pin 76 supported by the stationary frame 74 such that the pin 76 extends parallel to the x axis; an x-axis rotatable frame 78 that is supported by the pin 76 such that the x-axis rotatable frame 78 is rotatable about the pin 76; a spring 80 that biases the x-axis rotatable frame 78 in one direction about the pin 76; and an x-axis actuator 82 that biases the x-axis rotatable frame 78 in the opposite direction about the pin 76 so as to resist the biasing force of the spring 80. Thus, as shown in FIG. 6, the x-axis actuator 82 changes and selects a rotation position or posture of the two ultrasonic arrays A1, A2 about the x axis. The x-axis actuator 82 may be constituted by an electric motor or an electromagnetic solenoid. The z-axis rotating device 72 includes a worm wheel 84 which is supported by the x-axis rotatable frame 78 such that the worm wheel 84 is rotatable about the z axis and to which the two ultrasonic arrays A1, A2 are fixed via the substrate 68; a worm gear 86 that is engaged with an external thread of the worm wheel 84; and an electric motor 90 that is fixed to the x-axis rotatable frame 78 and has an output shaft 88 to which the worm gear 86 is fixed. As shown in FIG. 7, the z-axis rotating device 72 changes and selects a rotation position or posture of the two ultrasonic arrays A1, A2 about the z axis. The electric motor 90 functions as a z-axis actuator.

Figure 8:
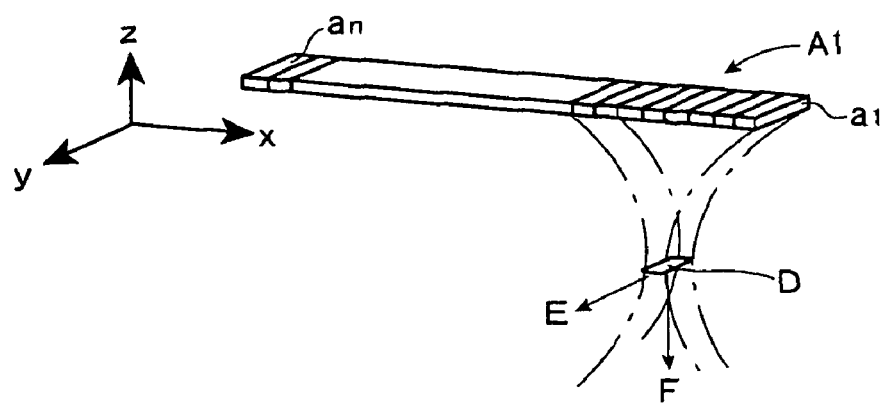
FIG. 8 is a view for explaining an ultrasonic beam (indicated by one-dot chain lines) generated by each of the ultrasonic arrays of the ultrasonic probe, and a convergent cross section, D, as a cross section of a convergent portion of the ultrasonic beam.
Figure 9:
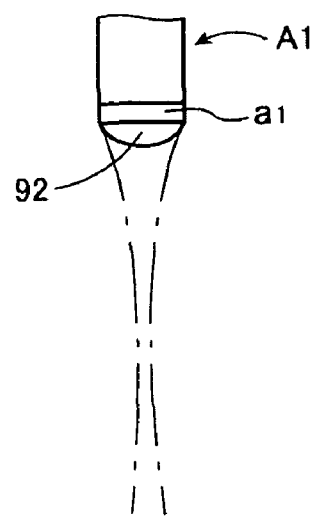
FIG. 9 is a view for explaining an acoustic lens provided for each of the ultrasonic arrays of the ultrasonic probe.

Back to FIG. 1, the ultrasonic-wave control circuit 38 carries out, according to a command supplied from the electronic control device 32, a beam-forming operation in which a predetermined number of transducers (e.g., 15 transducers) starting with one (e.g., transducer $a_1$) of opposite ends of each of the two ultrasonic arrays A1, A2 are simultaneously driven such that each of the transducers generates an ultrasonic wave having a frequency of about 10 MHz with a predetermined phase difference from the phase of the ultrasonic wave generated by each of the two transducers located adjacent the each transducer on either side of the same. While the predetermined number of transducers are shifted, one transducer by one, in a direction from the one end $a_1$ toward the other end an, each array A1, A2 sequentially generates, toward the blood vessel 20, respective ultrasonic beams each of which is convergent with respect to the direction of extension of the each array A1, A2, so as to scan the blood vessel 20. Each time each array A1, A2 generates the ultrasonic beam, it receives the ultrasonic beam reflected from the blood vessel 20, and inputs a signal representing the received, reflected ultrasonic beam to the control device 32. In FIG. 8, the convergent ultrasonic beam generated in the beam-forming operation is indicated by one-dot chain lines. In addition, as shown in FIG. 9, the outer surface of the free-end portion 24 in which each of the ultrasonic arrays A1, A2 is provided is covered with an acoustic lens 92 that causes the ultrasonic beams to converge with respect to a direction perpendicular to the direction of extension of the each array A1, A2. As shown in FIG. 8, the convergent ultrasonic beam generated by the cooperation of the beam-forming operation and the acoustic lens 92 has a convergent cross section, D, that is elongate in a direction, E, parallel to the direction perpendicular to the direction of extension of each array A1, A2. The lengthwise direction E of the convergent cross section D is perpendicular to the direction (i.e., x direction) of extension of each array A1, A2 and the direction (i.e., z direction), F, of generation of the convergent ultrasonic beam.

The electronic control device 32 synthesizes or produces, based on the signals representing the reflected ultrasonic beams, a transverse-cross-section image (i.e., a short-axis image) of the blood vessel 20 located under the skin surface 18, and/or a longitudinal-cross-section image (i.e., a long-axis image) of the blood vessel 20, and controls the monitor-image displaying device 34 to display the thus produced image(s) of the blood vessel 20. In addition, the control device 32 calculates, from the produced image(s) of the blood vessel 20, a diameter of the same 20, i.e., a diameter of the inner layer (tunica intima) of the same 20. Moreover, for the purpose of evaluating a function of the endothelium of the blood vessel 20, the control device 32 calculates a rate of change (%) [$=100 \times (d_{max}-d)/d$, where d is a diameter of the vessel 20 when the living being 14 is at rest; and $d_{max}$ is a maximum diameter of the vessel 20 after the flow of blood is resumed] of the diameter of the vessel 20 that represents FMD (flow-mediated dilation) following postischemia reactive hyperemia.

Figure 10:
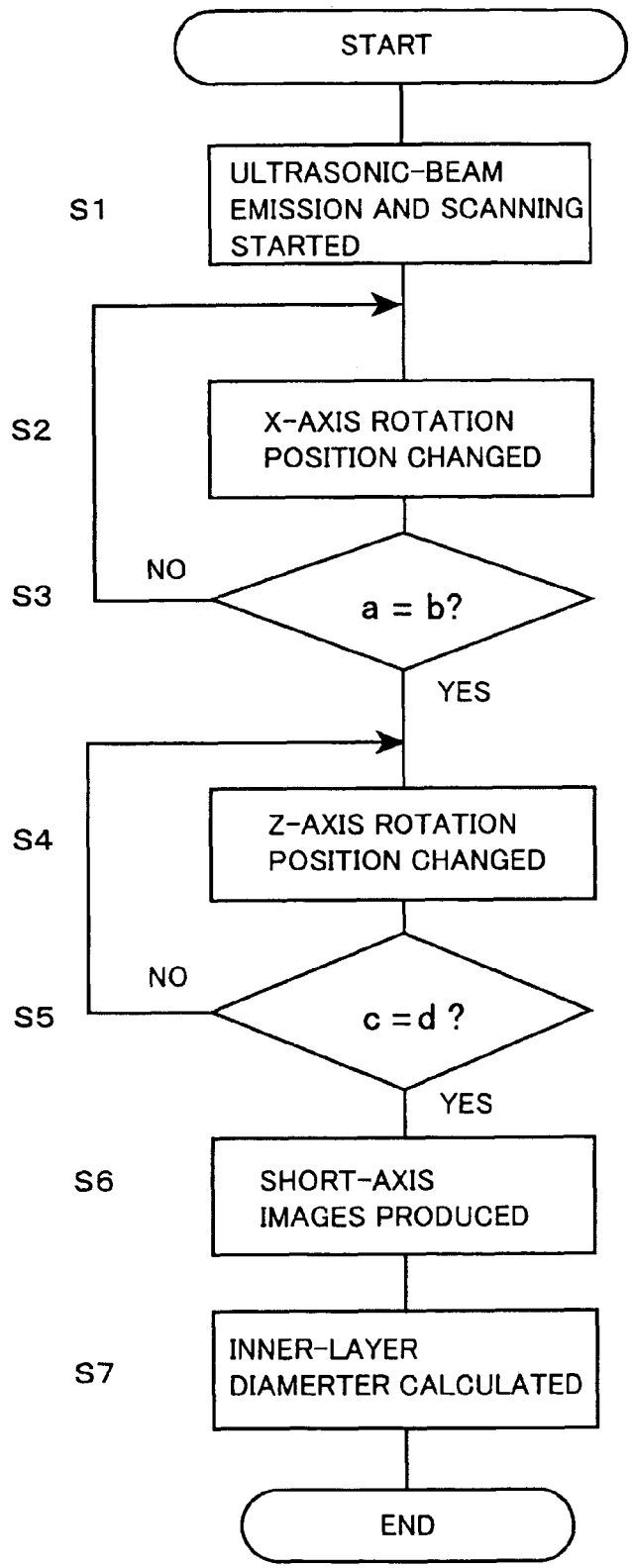
FIG. 10 is a flow chart representing relevant steps of a short-axis-image-production-related control operation of an electronic control device of the measuring apparatus of FIG. 1.
Figure 11:
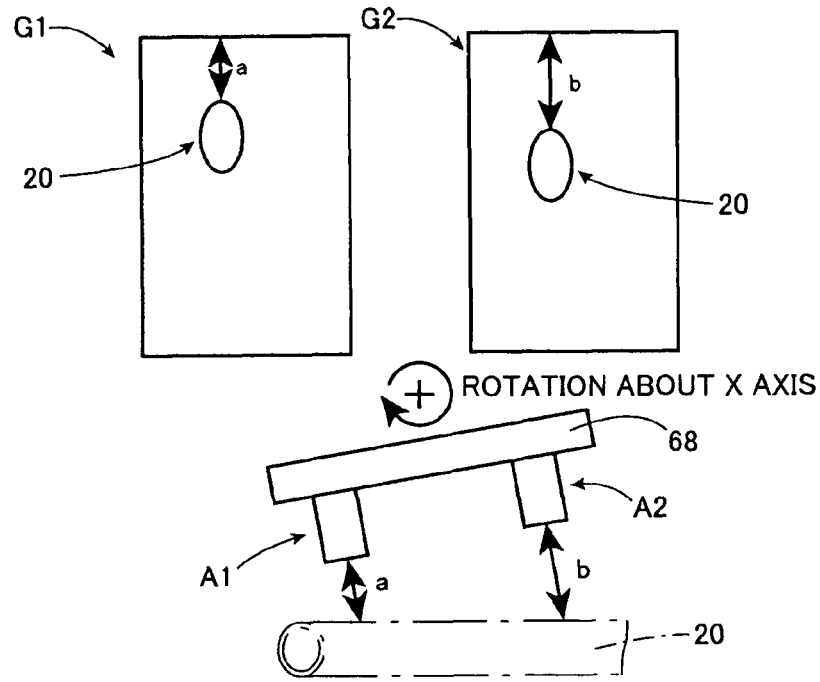
FIG. 11 is a view for explaining the control operation shown in FIG. 10, i.e., showing a relationship between respective rotation positions of the two ultrasonic arrays about the x axis and respective transverse cross-section images obtained by the two ultrasonic arrays in the case where respective distances between the two ultrasonic arrays and the blood vessel differ from each other.

FIG. 10 is a flow chart representing relevant steps of the operation of the electronic control device 32. First, at Step S1, ultrasonic beam emission and scanning are started. That is, the ultrasonic arrays A1, A2 emit the respective convergent ultrasonic beams to scan respective portions of the blood vessel 20 and obtain respective cross-section images G1, G2 shown in an upper portion of FIG. 11. Subsequently, at Step S2, the control device 32 calculates a distance, a, between the blood vessel 20 and a top side of a first rectangular display area displaying the cross-section image G1, and a distance, b, between the blood vessel 20 and a top side of a second rectangular display area displaying the cross-section image G2, and operates the x-axis actuator 82 to change, by a pre-set amount, a rotation position of the ultrasonic arrays A1, A2 about the x axis in a direction to decrease a difference of the two distances a, b. Step S2 is followed by Step S3 to judge whether the two distances a, b are equal to each other. As shown in a lower portion of FIG. 11, the distance a corresponds to a distance between the ultrasonic array A1 and the blood vessel 20, and the distance b corresponds to a distance between the ultrasonic array A2 and the blood vessel 20. Thus, Steps S2 and S3 correspond to an x-axis control means or device that controls respective postures of the ultrasonic arrays A1, A2 supported by the x-axis rotating device (i.e., the x-axis supporting device) 70, such that in the y-z plane, respective lengthwise directions of the respective convergent cross sections D of the respective ultrasonic beams emitted by the two ultrasonic arrays A1, A2 become parallel to a centerline of the blood vessel 20, i.e., such that in the y-z plane, respective beam-emission surfaces, S (FIG. 5), of the two ultrasonic arrays A1, A2 become parallel to the blood vessel 20 or the centerline thereof.

Figure 12:
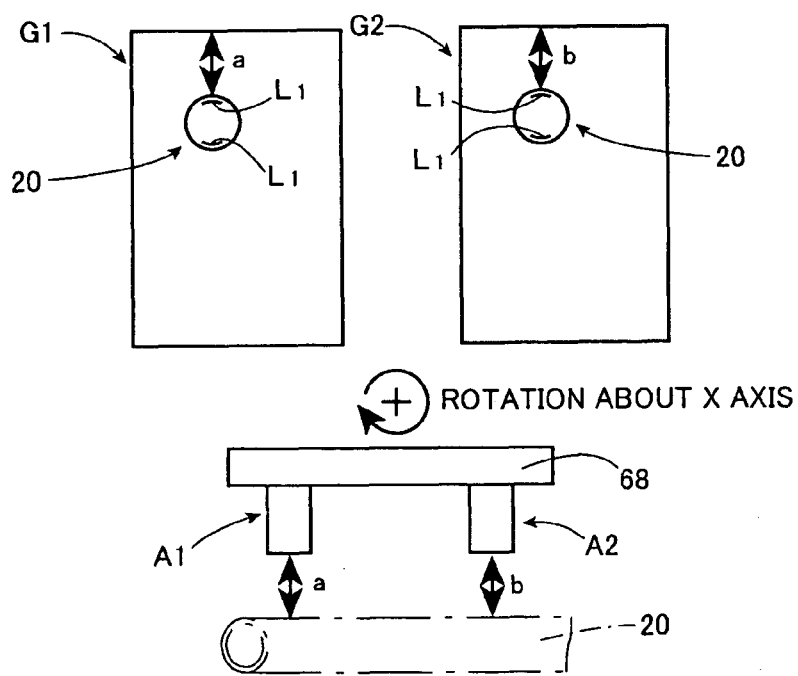
FIG. 12 is a view for explaining the control operation shown in FIG. 10, i.e., showing a relationship between respective rotation positions of the two ultrasonic arrays about the x axis and respective transverse cross-section images obtained by the two ultrasonic arrays in the case where respective distances between the two ultrasonic arrays and the blood vessel are equal to each other.

If a negative judgment is made at Step S3, Step S2 is repeated. Meanwhile, if a positive judgment is made at Step S3, it means that the two distances a, b are equal to each other. Thus, as shown in an upper portion of FIG. 12, each of the two cross-section images G1, G2 shows a circular image of the blood vessel 20 and, in the y-z plane, the respective beam-emission surfaces S of the two ultrasonic arrays A1, A2 are parallel to the blood vessel 20 or the centerline thereof. Therefore, the inner layer $L_1$ of the blood vessel 20 provides stronger reflection signals that form clearer images of the inner layer $L_1$ in the two cross-section images G1, G2.

Figure 13:
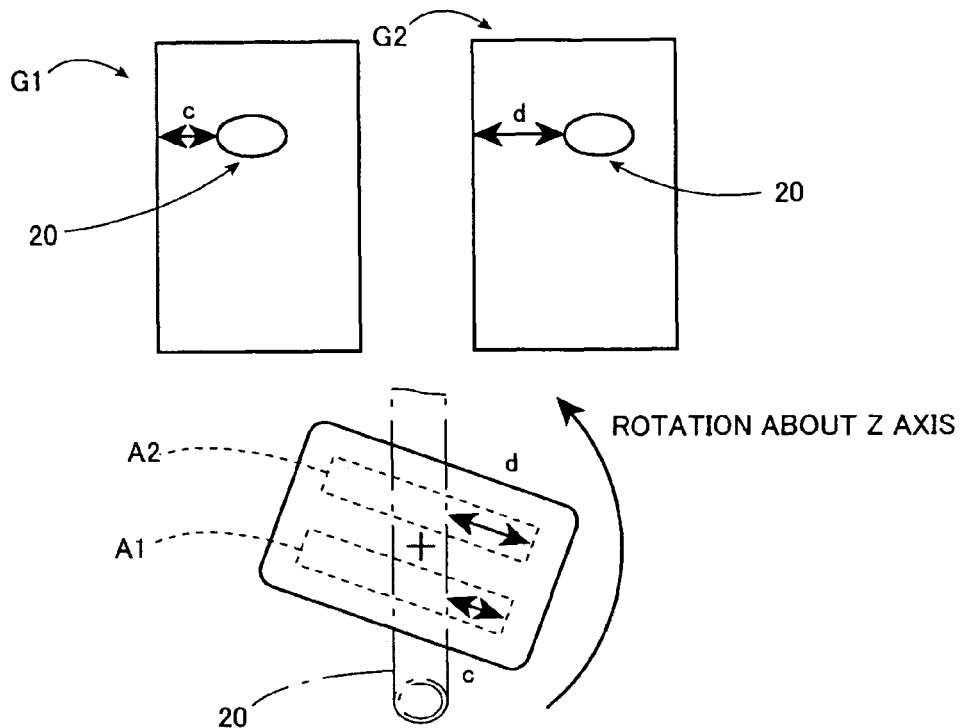
FIG. 13 is a view for explaining the control operation shown in FIG. 10, i.e., showing a relationship between respective rotation positions of the two ultrasonic arrays about the z axis and respective transverse cross-section images obtained by the two ultrasonic arrays in the case where the two ultrasonic arrays do not perpendicularly intersect the blood vessel.

At Step S4, the control device 32 calculates a distance, c, between the blood vessel 20 and a left side of the first rectangular display area displaying the ultrasonic cross-section image G1, and a distance, d, between the blood vessel 20 and a left side of the second rectangular display area displaying the ultrasonic cross-section image G2, as shown in an upper portion of FIG. 13, and operates the electric motor 90 as the z-axis actuator to change, by a pre-set amount, a rotation position of the ultrasonic arrays A1, A2 about the z axis in a direction to decrease a difference of the two distances c, d. Step S4 is followed by Step S5 to judge whether the two distances c, d are equal to each other. As shown in a lower portion of FIG. 13, the distance c corresponds to a distance between one end of the ultrasonic array A1 and the blood vessel 20, and the distance d corresponds to a distance between a corresponding end of the ultrasonic array A2 and the blood vessel 20. Thus, Steps S4 and S5 correspond to a z-axis control means or device that controls respective postures of the ultrasonic arrays A1, A2 supported by the z-axis rotating device (i.e., the z-axis supporting device) 72, such that in the x-y plane, respective lengthwise directions of the respective convergent cross sections D of the respective ultrasonic beams emitted by the two ultrasonic arrays A1, A2 become parallel to the centerline of the blood vessel 20, i.e., such that in the x-y plane, the respective beam-emission surfaces S of the two ultrasonic arrays A1, A2 become parallel to the blood vessel 20 or the centerline thereof.

Figure 14:
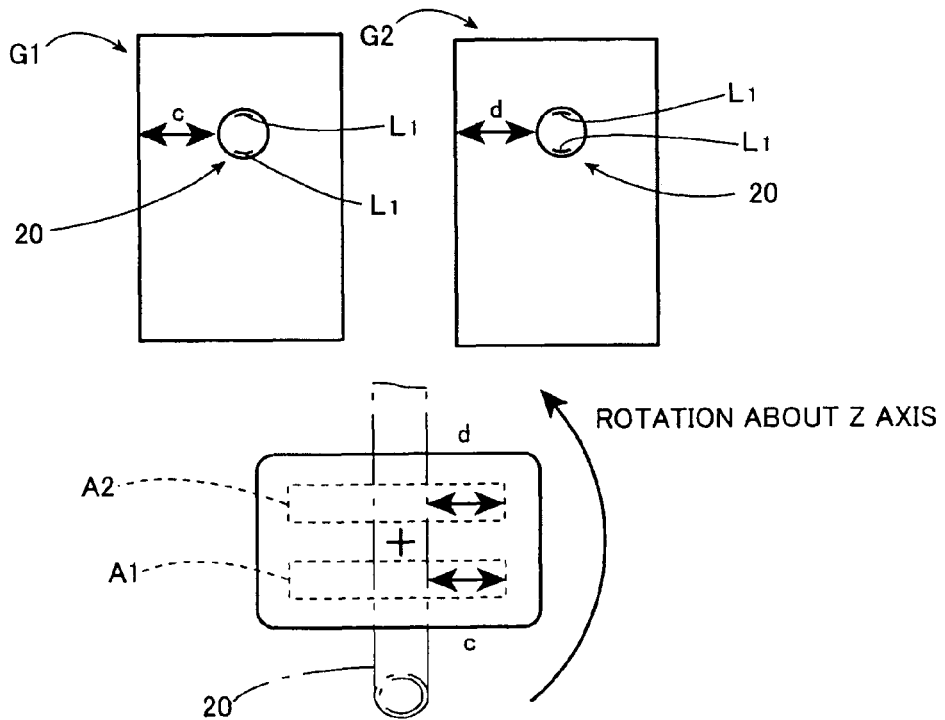
FIG. 14 is a view for explaining the control operation shown in FIG. 10, i.e., showing a relationship between respective rotation positions of the two ultrasonic arrays about the z axis and respective transverse cross-section images obtained by the two ultrasonic arrays in the case where the two ultrasonic arrays perpendicularly intersect the blood vessel.

If a negative judgment is made at Step S5, Step S4 is repeated. Meanwhile, if a positive judgment is made at Step S5, it means that the two distances c, d are equal to each other. Thus, as shown in an upper portion of FIG. 14, each of the two cross-section images G1, G2 shows a circular image of the blood vessel 20 and, in the x-y plane, the respective beam-emission surfaces S of the two ultrasonic arrays A1, A2 are parallel to the blood vessel 20 or the centerline thereof. Therefore, the inner layer $L_1$ of the blood vessel 20 provides stronger reflection signals that form clearer images of the inner layer $L_1$ in the two cross-section images G1, G2.

At Step S6, the control device 32 produces the two cross-section images G1, G2 of the blood vessel 20, i.e., two short-axis images thereof, operates the monitor-image displaying device 34 to display the thus produced short-axis images of the blood vessel 20, and stores, in a memory thereof, image data representing the thus produced short-axis images. Subsequently, at Step S7, the control device 32 calculates a diameter of the inner layer $L_1$ of the blood vessel 20 shown in each of the two-short-axis images thereof.

As is apparent from the foregoing description of the blood-vessel-image measuring apparatus 22, the ultrasonic probe 12 employs the main frame 28 adapted to be placed on the living being 14, and the x-axis rotating device (the x-axis supporting device) 70 that is supported by the main frame 28 and that supports the two ultrasonic arrays A1, A2 such that the arrays A1, A2 are rotatable about the x axis parallel to the direction of extension of the arrays A1, A2, i.e., the direction of arrangement of the ultrasonic transducers $a_1, a_2, \ldots, a_n$ in each array A1, A2. In addition, the measuring apparatus 22 includes the x-axis control means or device S2, S3 that controls the respective postures of the two ultrasonic arrays A1, A2 supported by the x-axis rotating device 70, such that in the y-z plane, the respective beam-emission surfaces S of the arrays A1, A2 become parallel to the blood vessel 20 or the centerline thereof. That is, the two ultrasonic arrays A1, A2 obtain the respective ultrasonic beams reflected from the blood vessel 20, in the state in which the respective lengthwise directions of the respective convergent cross sections D of the respective ultrasonic beams emitted by the two arrays A1, A2 are parallel to the centerline of the blood vessel 20. Based on the thus obtained, reflected ultrasonic beams, the control device 32 can obtain highly clear and accurate transverse cross-section images of the blood vessel 20.

Moreover, in the blood-vessel-image measuring apparatus 22, the ultrasonic probe 12 employs the main frame 28 adapted to be placed on the living being 14, and the z-axis rotating device (the z-axis supporting device) 72 that is supported by the main frame 28 and that supports the two ultrasonic arrays A1, A2 such that the arrays A1, A2 are rotatable about the z axis perpendicular to the respective beam-emission surfaces S of the arrays A1, A2, i.e., the outer surface of the skin 18. In addition, the measuring apparatus 22 includes the z-axis control means or device S4, S5 that controls the respective postures of the two ultrasonic arrays A1, A2 supported by the z-axis rotating device 72, such that in the x-y plane, the respective beam-emission surfaces S of the arrays A1, A2 become parallel to the blood vessel 20 or the centerline thereof. That is, the two ultrasonic arrays A1, A2 obtain the respective ultrasonic beams reflected from the blood vessel 20, in the state in which the respective lengthwise directions of the respective convergent cross sections D of the respective ultrasonic beams emitted by the two arrays A1, A2 are parallel to the centerline of the blood vessel 20. Based on the thus obtained, reflected ultrasonic beams, the control device 32 can obtain highly clear and accurate transverse cross-section images of the blood vessel 20.

Next, there will be described a second embodiment of the present invention by reference to FIGS. 15 through 21. The same reference numerals as used in the first embodiment shown in FIGS. 1 through 14 are used to designate the corresponding elements or parts of the second embodiment, and the description thereof is omitted.

Figure 15:
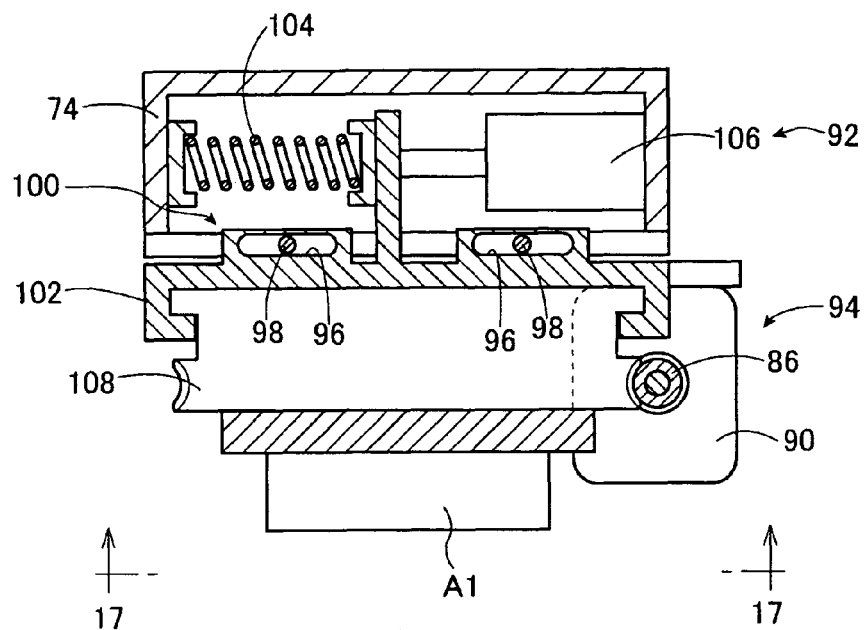
FIG. 15 is a cross-section view for explaining another multiple-axis driving or positioning device of another ultrasonic probe employed by another blood-vessel-image measuring apparatus as a second embodiment of the present invention, the multiple-axis positioning device including an x-axis moving device and a z-axis rotating device.
Figure 16:
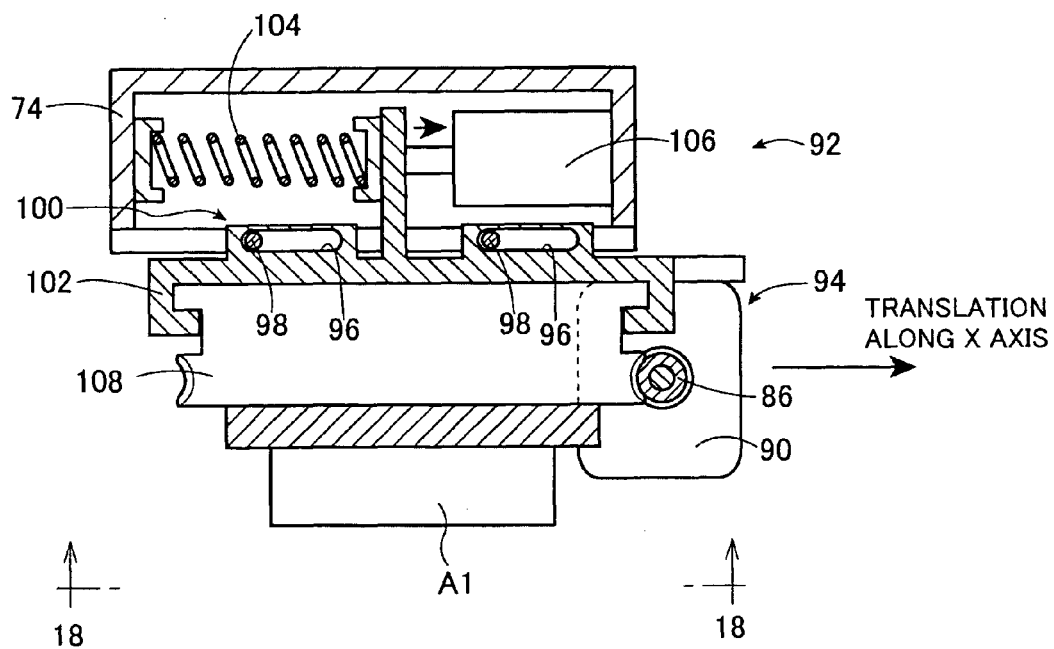
FIG. 16 is a cross-section view showing a state in which an x-axis-direction position of ultrasonic arrays of the ultrasonic probe has been changed by the x-axis moving device of FIG. 15.
Figure 17:
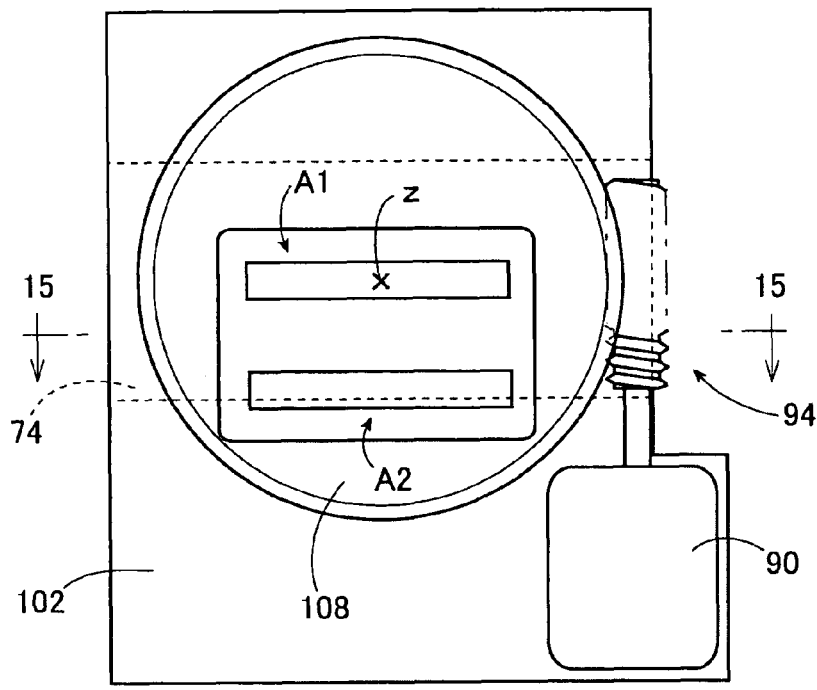
FIG. 17 is a bottom view for explaining the multiple-axis positioning device of the ultrasonic probe of FIG. 15 that includes the x-axis moving device and the z-axis rotating device and positions the ultrasonic arrays relative to a blood vessel.
Figure 18:
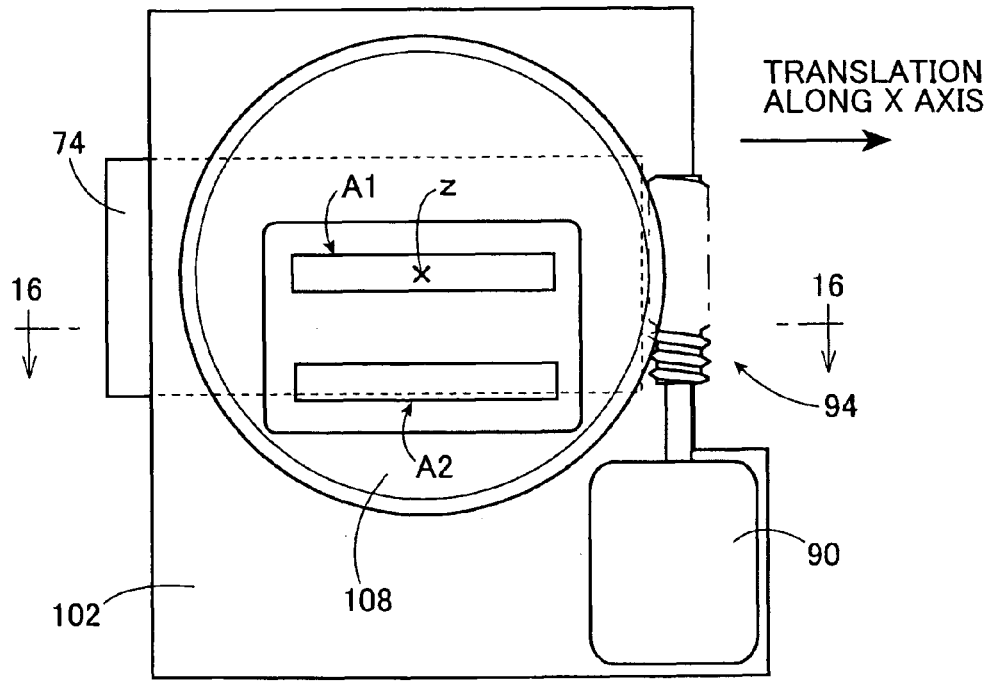
FIG. 18 is a view showing a state in which an x-axis-direction position of the ultrasonic arrays of the ultrasonic probe has been changed by the x-axis moving device of FIG. 15.

The second embodiment relates to a blood-vessel-image measuring apparatus that employs a different multiple-axis driving or positioning device than the multiple-axis driving or positioning device 26 used in the first embodiment. As shown in FIGS. 15 through 18, the present multiple-axis positioning device includes an x-axis moving device 92 functioning as an x-axis supporting device that is supported by the main frame 28 and that supports the two ultrasonic arrays A1, A2 such that the arrays A1, A2 can be translated in an x-axis direction parallel to the direction of arrangement of the ultrasonic transducers $a_1, a_2, \ldots, a_n$ in each array A1, A2; and a z-axis rotating device 94 functioning as a z-axis supporting device that is supported by the main frame 28 and that supports the two ultrasonic arrays A1, A2 such that the arrays A1, A2 are rotatable about a z axis that is perpendicular to the respective beam-emission surfaces S of the arrays A1, A2, i.e., the outer surface of the skin 18 and that passes through one A1 of the two arrays A1, A2. The x-axis moving device 92 includes a guide device 100 having elongate guide holes 96 and two guide pins 98 that fit in the guide holes 96 and cooperate with the same 96 to support a movable frame 102 such that the movable frame 102 is linearly movable relative to the stationary frame 74 in the x-axis direction; a spring 104 that biases the movable frame 102 in one direction parallel to the x-axis direction; and an x-axis actuator 106 that biases the movable frame 102 in the opposite direction, against the biasing force of the spring 104. Thus, the x-axis moving device 92 changes and selects a position of the two ultrasonic arrays A1, A2 in the x-axis direction. The x-axis actuator 106 may be constituted by an electric motor or an electromagnetic solenoid. The z-axis rotating device 94 includes a worm wheel 108 which is supported by the movable frame 102 such that the worm wheel 108 is rotatable about the z axis passing through a lengthwise middle portion of the ultrasonic array A1 and to which the two ultrasonic arrays A1, A2 are fixed via the substrate 68; a worm gear 86 that is engaged with an external thread of the worm wheel 108; and an electric motor 90 that is fixed to the movable frame 102 and has an output shaft 88 to which the worm gear 86 is fixed. The z-axis rotating device 94 changes and selects a rotation position or posture of the two ultrasonic arrays A1, A2 about the z axis passing through the ultrasonic array A1. The electric motor 90 functions as a z-axis actuator. FIGS. 15 and 17 show a state in which the movable frame 102 is positioned at a middle position of a movement range thereof in the x-axis direction; and FIGS. 16 and 18 show a state in which the movable frame 102 is positioned at one end of the movement range thereof in the x-axis direction.

Figure 19:
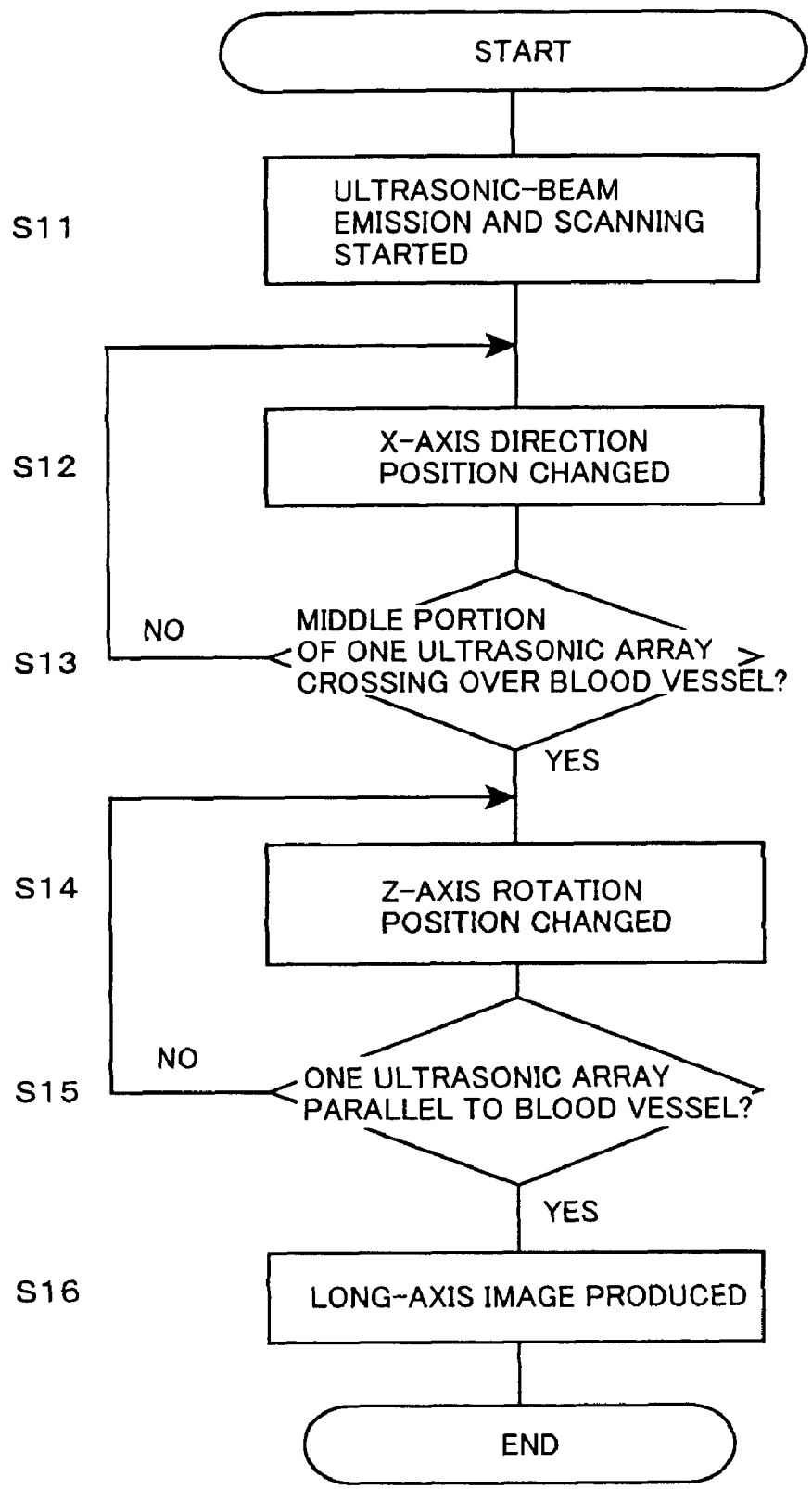
FIG. 19 is a flow chart representing relevant steps of a long-axis-image-production-related control operation of an electronic control device of the measuring apparatus of FIG. 15.
Figure 20:
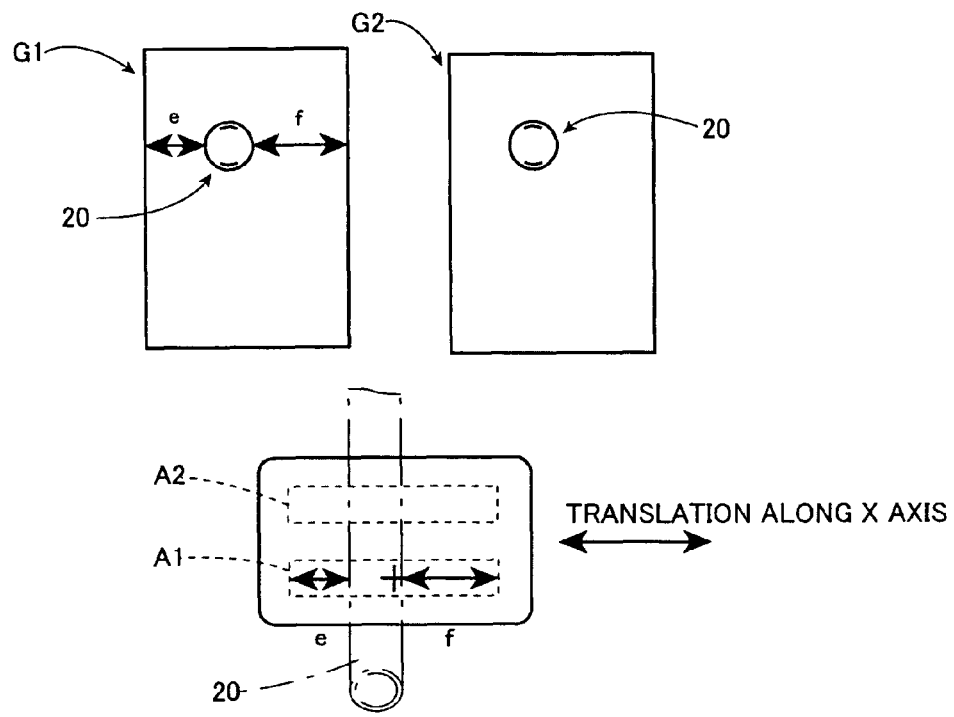
FIG. 20 is a view for explaining the control operation shown in FIG. 19, i.e., showing a relationship between respective x-axis-direction positions of two ultrasonic arrays and respective transverse cross-section images obtained by the two ultrasonic arrays in the case where the two ultrasonic arrays intersect the blood vessel.

FIG. 19 is a flow chart representing relevant steps of an operation of an electronic control device 32 employed in the second embodiment. First, at Step S11, ultrasonic-beam emission and scanning are started. That is, the two ultrasonic arrays A1, A2 emit the respective convergent ultrasonic beams to scan respective portions of the blood vessel 20 and obtain respective cross-section images G1, G2 shown in an upper portion of FIG. 20. Subsequently, at Step S12, the control device 32 calculates a distance, e, between the blood vessel 20 and a left side of the first rectangular display area displaying the cross-section image G1, and a distance, f, between the blood vessel 20 and a right side of the first rectangular display area, and operates the x-axis actuator 106 to change, by a pre-set amount, a position of the ultrasonic arrays A1, A2 with respect to the x-axis direction, in a direction to decrease a difference of the two distances e, f. Step S12 is followed by Step S13 to judge whether the two distances e, f are equal to each other. As shown in a lower portion of FIG. 20, the distance $\underline{e}$ corresponds to a distance between one of opposite ends of the ultrasonic array A1 and the blood vessel 20, and the distance $\underline{f}$ corresponds to a distance between the other end of the ultrasonic array A1 and the blood vessel 20. Thus, at Steps S12 and S13, the control device 32 operates the x-axis moving device 92 to move and position the ultrasonic array A1, such that a lengthwise middle position of the array A1 crosses over the blood vessel 20.

If a negative judgment is made at Step S13, Step S12 is repeated. Meanwhile, if a positive judgment is made at Step S13, it means that the middle position of the ultrasonic array A1 crosses over the blood vessel 20. Subsequently, at Step S14, the control device 32 operates the electric motor 90 as the z-axis actuator to change, by a pre-set amount, a rotation position of the ultrasonic arrays A1, A2 about the z axis. Step S14 is followed by Step S15 to judge whether the ultrasonic array A1 is parallel to the blood vessel 20. If a negative judgment is made at Step S15, Step S14 is repeated to continue rotating the array A1 till a positive judgment is made at Step S15. Thus, Steps S12 through S15 correspond to a y-z-axis control means or device that controls the x-axis moving device (i.e., the x-axis supporting device) 92 to move and position the ultrasonic array A1 such that the middle portion of the array A1 through which the z axis passes is positioned right above the blood vessel 20, and subsequently controls the z-axis rotating device (i.e., the z-axis supporting device) 94 to rotate and position the array A1 such that the direction of extension of the array A1 is parallel to the blood vessel 20.

Figure 21:
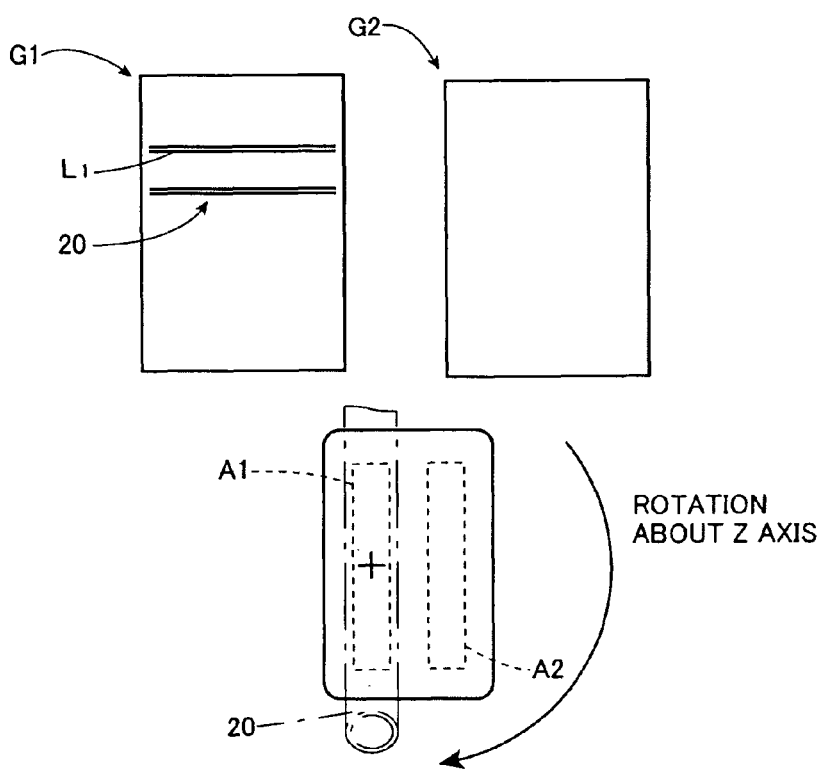
FIG. 21 is a view for explaining the control operation shown in FIG. 10, i.e., showing a relationship between respective x-axis-direction positions of the two ultrasonic arrays and a longitudinal cross-section image obtained by one of the two ultrasonic arrays in the case where the one ultrasonic array is positioned right above the blood vessel and extends parallel to the same.

If a positive judgment is made at Step S15, it means that a longitudinal axis of the ultrasonic array A1 is aligned with the centerline of the blood vessel 20 and is positioned right above the same 20, as shown in a lower portion of FIG. 21. Thus, as shown in an upper portion of FIG. 21, the cross-section image G1 corresponding to the ultrasonic array A1 shows a longitudinal cross section of the blood vessel 20. In this state, the lengthwise direction of the convergent cross section D of the ultrasonic beam emitted by the ultrasonic array A1 is perpendicular to the centerline of the blood vessel 20, and the beam-emission surface S of the array A1 is parallel to the blood vessel 20. Therefore, the inner layer $L_1$ of the blood vessel 20 provides stronger reflection signals that form a clearer image of the inner layer $L_1$ in the cross-section image G1.

As is apparent from the foregoing description of the blood-vessel-image measuring apparatus as the second embodiment, the ultrasonic probe 12 employs the main frame 28 adapted to be placed on the living being 14, and the x-axis moving device (the x-axis supporting device) 92 that is supported by the main frame 28 and that supports the ultrasonic arrays A1, A2 such that the arrays A1, A2 are movable or translatable in the x-axis direction parallel to the direction of arrangement of the ultrasonic transducers $a_1, a_2, \ldots, a_n$ in each array A1, A2. In addition, the probe 12 employs the z-axis rotating device (the z-axis supporting device) 94 that is supported by the main frame 28 and that supports the ultrasonic array A1 such that the array A1 is rotatable about the z axis that is perpendicular to the beam-emission surface S of the array A1, i.e., the outer surface of the skin 18 and that passes through the array A1. Moreover, the present measuring apparatus includes the y-z-axis control means or device (S12 through S15) that controls the x-axis moving device 92 to move and position the ultrasonic array A1 such that the middle portion of the array A1 through which the z axis passes is positioned right above the blood vessel 20, and subsequently controls the z-axis rotating device 94 to rotate and position the array A1 such that the direction of extension of the array A1 is parallel to the blood vessel 20. Since the portion of the array A1 through which the z axis passes is positioned right above the blood vessel 20, and the direction of extension of the array A1 is parallel to the blood vessel 20, the control device 32 can obtain, based on the ultrasonic beams reflected from the blood vessel 20, a highly clear and accurate longitudinal cross-section image of the blood vessel 20.

Figure 22:
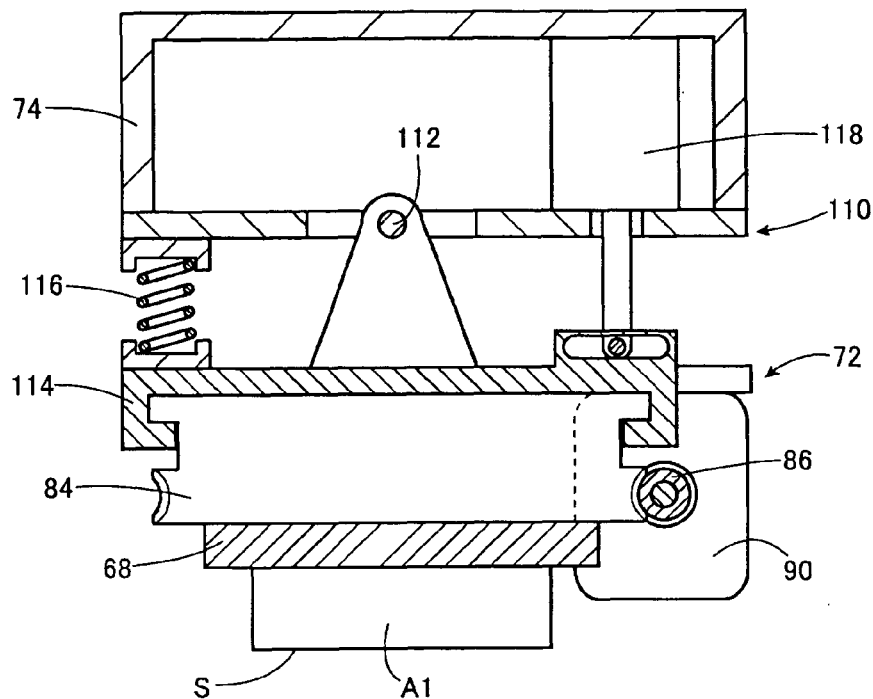
FIG. 22 is a cross-section view for explaining another multiple-axis driving or positioning device of another ultrasonic probe employed by another blood-vessel-image measuring apparatus as a third embodiment of the present invention, the multiple-axis positioning device including a y-axis rotating device and a z-axis rotating device that cooperate with each other to position two ultrasonic arrays relative to a blood vessel.
Figure 23:
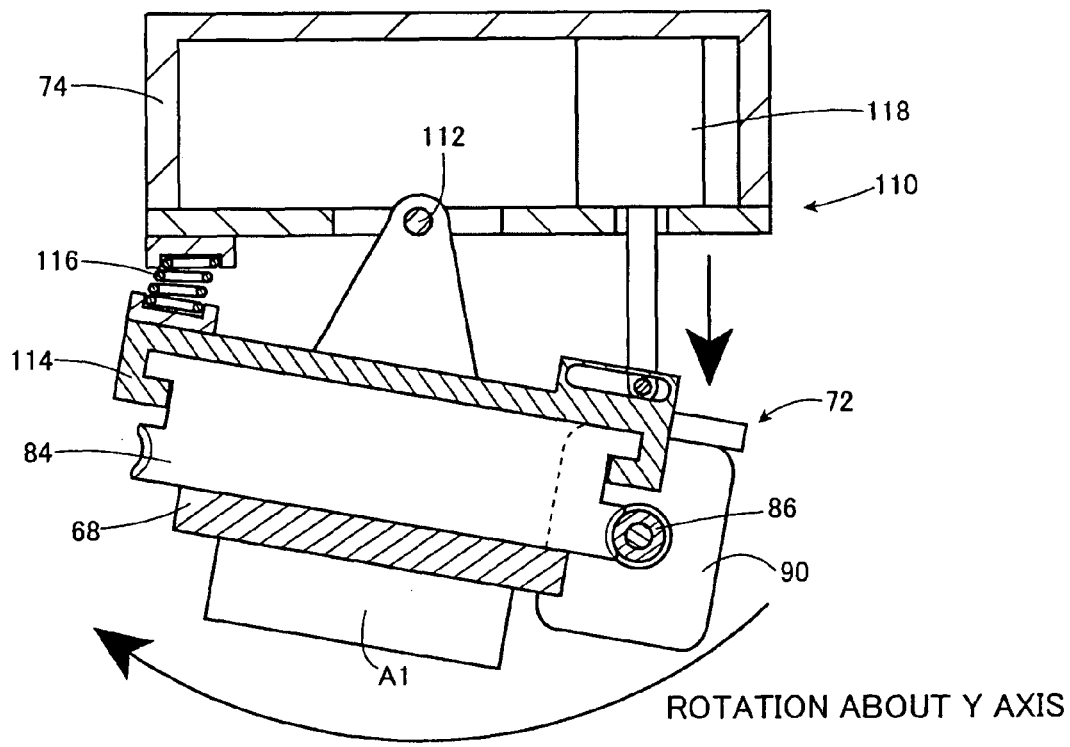
FIG. 23 is a cross-section view showing a state in which a rotation position of the ultrasonic arrays has been changed by the y-axis rotating device of FIG. 22.

Next, there will be described a third embodiment of the present invention by reference to FIGS. 22 through 26. The same reference numerals as used in the first embodiment shown in FIGS. 1 through 14 are used to designate the corresponding elements or parts of the second embodiment, and the description thereof is omitted. The third embodiment relates to a blood-vessel-image measuring apparatus that employs a different multiple-axis driving or positioning device than the multiple-axis driving or positioning device 26 used in the first embodiment. As shown in FIGS. 22 and 23, the present multiple-axis positioning device includes a y-axis rotating device 110 that changes and selects a rotation position of the two ultrasonic arrays A1, A2 about the y axis; and a z-axis rotating device 72 (FIG. 5) that changes and selects a rotation position of the two ultrasonic arrays A1, A2 about the z axis. The y-axis rotating device 110 functions as a y-axis supporting device that supports the two ultrasonic arrays A1, A2 such that the two ultrasonic arrays A1, A2 are rotatable about the y axis parallel to the blood vessel 20. The y-axis rotating device 110 includes a stationary frame 74 fixed to a lower end of the main frame 28; a pin 112 supported by the stationary frame 74 such that the pin 112 extends parallel to the y axis; a y-axis rotatable frame 114 that is supported by the pin 112 such that the y-axis rotatable frame 114 is rotatable about the pin 112; a spring 116 that biases the y-axis rotatable frame 114 in one direction about the pin 112; and a y-axis actuator 118 that biases the y-axis rotatable frame 114 in the opposite direction about the pin 112, against the biasing force of the spring 116. Thus, as shown in FIG. 23, the y-axis actuator 118 changes and selects a rotation position or posture of the two ultrasonic arrays A1, A2 about the y axis. The y-axis actuator 118 may be constituted by an electric motor or an electromagnetic solenoid. The z-axis rotating device 72 is supported by the y-axis rotatable frame 114.

Figure 24:
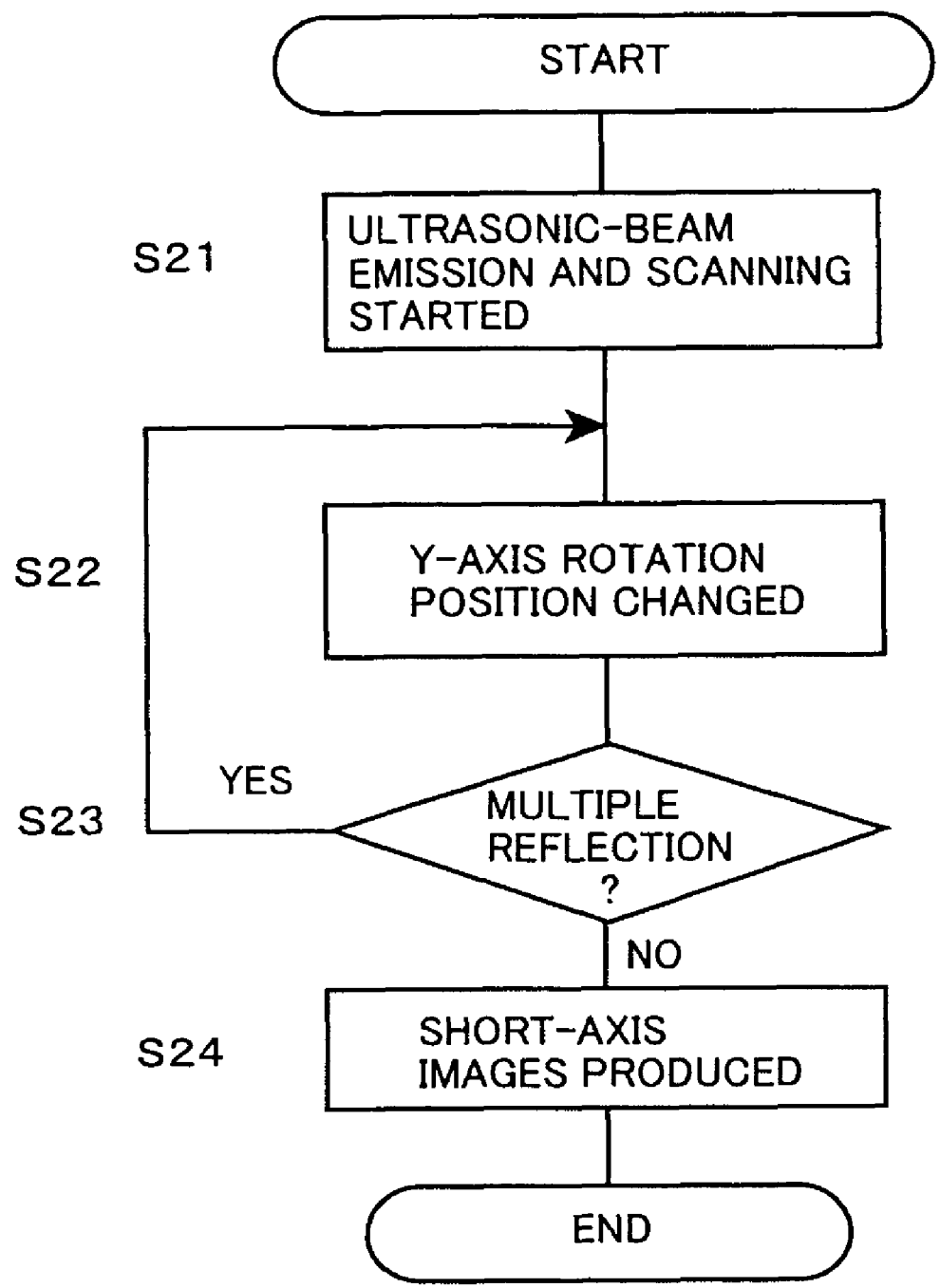
FIG. 24 is a flow chart representing relevant steps of a short-axis-image-production-related control operation of an electronic control device of the measuring apparatus of FIG. 22.
Figure 25:
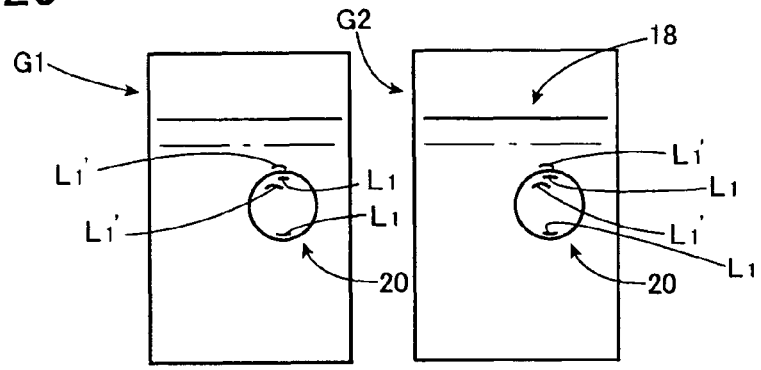
FIG. 25 is a view for explaining the control operation shown in FIG. 24, i.e., showing a relationship between respective rotation positions of the two ultrasonic arrays about the y axis and respective transverse cross-section images obtained by the two ultrasonic arrays in the case where respective emission surfaces of the two ultrasonic arrays are parallel to a surface of the skin.
Figure 25:
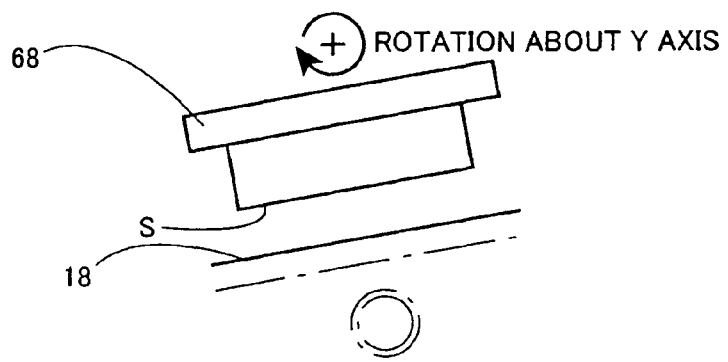
Figure 26:
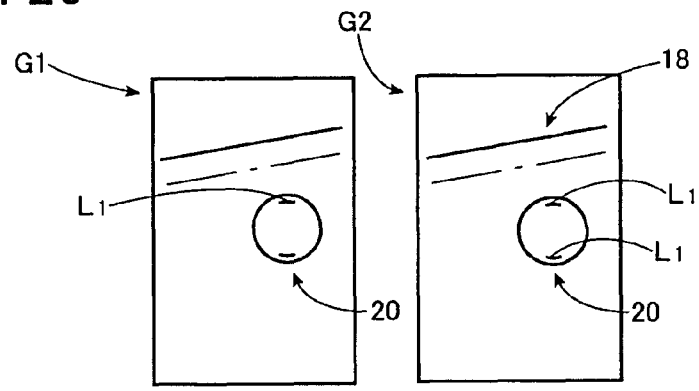
FIG. 26 is a view for explaining the control operation shown in FIG. 24, i.e., showing a relationship between respective rotation positions of the two ultrasonic arrays about the y axis and respective transverse cross-section images obtained by the two ultrasonic arrays in the case where the respective emission surfaces of the two ultrasonic arrays are inclined by an appropriate angle, α, relative to the surface of the skin.
Figure 26:
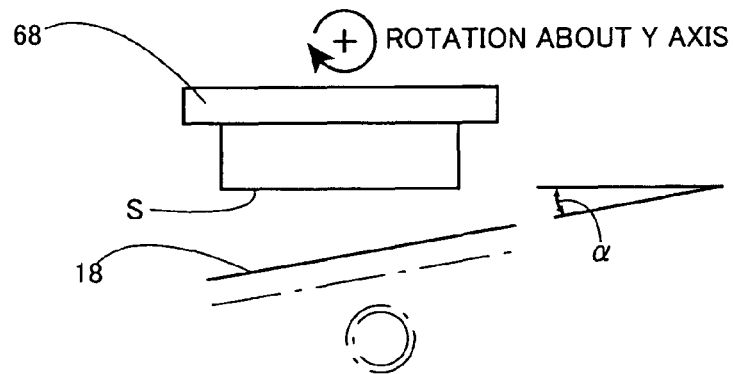

FIG. 24 is a flow chart representing relevant steps of an operation of an electronic control device 32 employed in the third embodiment. First, at Step S21, ultrasonic-beam emission and scanning are started. That is, the two ultrasonic arrays A1, A2 emit respective convergent ultrasonic beams to scan respective portions of the blood vessel 20 and obtain respective ultrasonic cross-section images G1, G2, as shown in an upper portion of FIG. 25. The ultrasonic cross-section images G1, G2 are displayed by the monitor-image displaying device 34. Subsequently, at Step S22, if the two short-axis images G1, G2, displayed by the displaying device 34, have respective ghost images $L_1'$ of the inner layer $L_1$ that are caused by the multiple reflection produced between the skin surface 18 and the blood vessel 20, a rotation angle of the ultrasonic arrays A1, A2 about the y axis is changed by a predetermined angle in a direction to solve the multiple reflection. Then, at Step S23, whether the two short-axis images G1, G2 have respective ghost images $L_1'$ is judged automatically or manually. In the case of the automatic judgment, for example, whether respective lumens of the blood vessels 20 in the cross-section images G1, G2 displayed by the displaying device 34 have respective degrees of luminance each lower than a reference degree because of absence of ghost images $L_1'$ from the images G1, G2, is judged. If the respective lumens of the blood vessels 20 in the cross-section images G1, G2 have respective ghost images $L_1'$ caused by the multiple reflection, then those lumens look lighter on the displaying device 34 and accordingly have a higher degree of luminance. On the other hand, if the respective lumens of the blood vessels 20 do not have ghost images $L_1'$, then those lumens look darker.

At Step S22, the rotation angle of the ultrasonic arrays A1, A2 about the y axis is selected by an operator, by operating a manually operable input device, i.e., the keyboard 36 and/or the mouse 37, so as to control the y-axis rotating device 110 such that as the ghost images $L_1'$ caused by the multiple reflection are effectively prevented, clearer short-axis images of the blood vessel 20 are obtained, i.e., the respective emission surfaces S of the two ultrasonic arrays A1, A2 become more parallel to the skin surface 18. Thus, at Step S22, the emission surfaces S of the ultrasonic arrays A1, A2 and the skin surface 18 can contain, therebetween, an angle, α, assuring that the ghost images $L_1'$ caused by the multiple reflection are prevented from being formed in the short-axis images of the blood vessel 20. In the present embodiment, Step S22 corresponds to an emission-surface-angle controlling step where the rotation angle of the ultrasonic arrays A1, A2 about the y axis is changed.

If a positive judgment is made at Step S23, then Step S22 is repeated. Meanwhile, If a negative judgment is made at Step S23, it means that the ghost images $L_1'$ caused by the multiple reflection are effectively prevented. Then, the control of the control device 32 goes to Step S24 to obtain clear transverse cross-section images (i.e., short-axis images) of the blood vessel 20. Based on the clear short-axis images of the blood vessel 20, an accurate diameter of the inner layer $L_1$ of the blood vessel 20 can be calculated.

As is apparent from the foregoing description of the blood-vessel-image measuring apparatus as the third embodiment, the ultrasonic probe 12 employs the main frame 28 adapted to be placed on the living being 14, and the y-axis rotating device (the y-axis supporting device) 110 that is supported by the main frame 28 and that supports the ultrasonic arrays A1, A2 such that the arrays A1, A2 are rotatable about the y axis perpendicular to the direction of arrangement of the ultrasonic transducers $a_1, a_2, \ldots, a_n$ in each array A1, A2. In addition, the control device 32 employs Steps S22 and S23 where the rotation posture or angle of the y-axis rotating device 110 is changed to provide, between the emission surfaces S and the skin surface 18 opposed to the same S, the angle α assuring that the ghost images $L_1'$ caused by the multiple reflection are prevented from being formed in the cross-section images of the blood vessel 20. Thus, the emission surfaces S of the ultrasonic arrays A1, A2 are inclined by the angle α relative to the outer surface of the skin 18, so as to prevent the multiple reflection, and accordingly highly clear and accurate transverse cross-section (i.e., short-axis) images of the endothelium (i.e., the inner layer $L_1$) of the blood vessel 20 are obtained.

In the first embodiment shown in FIGS. 1 through 14, the rotation of the two ultrasonic arrays A1, A2 about the x axis is automatically carried out at Steps S2 and S3 of FIG. 10; and the rotation of the ultrasonic arrays A1, A2 about the z axis is automatically carried out at Steps S4 and S5 of FIG. 10. However, the rotation of the ultrasonic arrays A1, A2 about each of the x axis and the z axis may be controlled in a manual operation.

Figure 27:
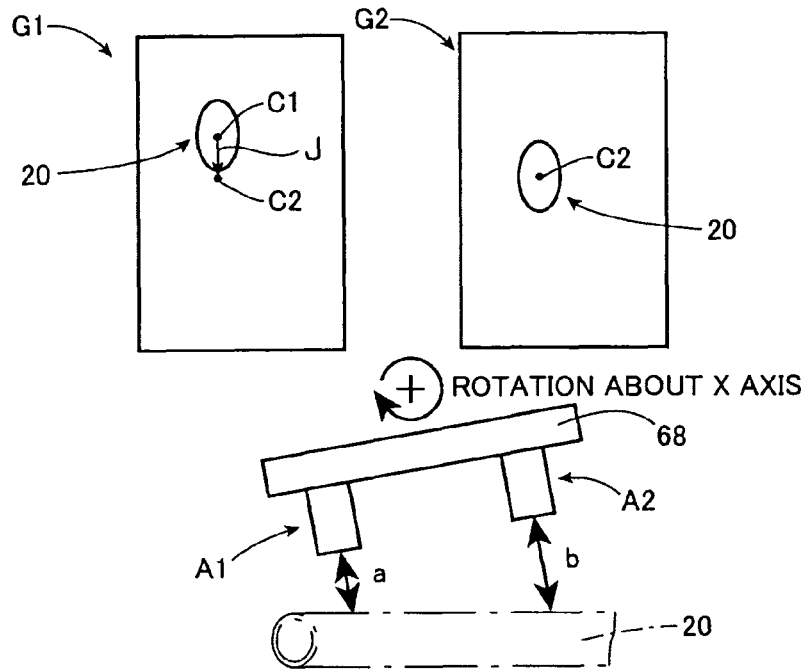
FIG. 27 is a view showing an image displayed by a displaying device employed by another blood-vessel-image measuring apparatus as a modified embodiment of the first embodiment, the displayed image being used in a manual control operation in which respective distances between the two ultrasonic arrays and the blood vessel in the z-axis direction are made equal to each other by manually operating an input device, and showing an arrow indicating a rotation direction about the x axis in which the x-axis rotating device is rotated to cause respective center positions, C1, C2, of respective images of the blood vessel obtained by the two ultrasonic arrays, to coincide with each other in the z-axis direction and thereby zero the difference of the two distances.
Figure 28:
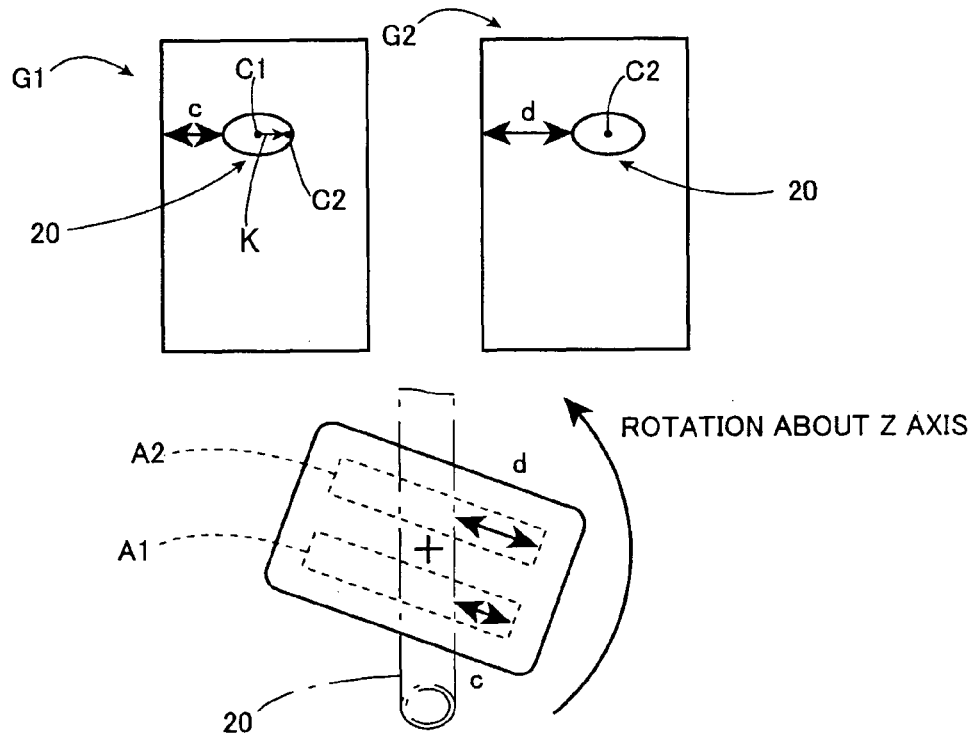
FIG. 28 is a view showing image displayed by the displaying device employed in the modified embodiment of the first embodiment, the displayed image being used in a manual control operation in which respective distances between the two ultrasonic arrays and the blood vessel in the x-axis direction are made equal to each other by manually operating the input device, and showing an arrow indicating a rotation direction about the z axis in which the z-axis rotating device is rotated to cause respective center positions, C1, C2, of respective images of the blood vessel obtained by the two ultrasonic arrays, to coincide with each other in the x-axis direction and thereby zero the difference of the two distances.

In a modified form of the first embodiment, Step S2 of FIG. 10 is replaced with a step where the monitor-image displaying device 34 displays, as shown in an upper portion of FIG. 27, respective ultrasonic cross-section images G1, G2, obtained by the two ultrasonic arrays A1, A2, such that respective center positions of the blood vessel 20 in the z axis are indicated or designated by respective symbols, C1, C2, and an arrow, J, representing a rotation direction, about the x axis, in which the x-axis rotating device 70 is rotated to zero the difference of the two center positions C1, C2. According to the symbols C1, C2 and the arrow J, displayed by the displaying device 34, an operator manually operates a manually operable input device, i.e., the keyboard 36 and/or the mouse 37 so as to control manually the x-axis rotating device 70 and thereby select a rotation angle of the ultrasonic arrays A1, A2 about the x axis. In addition, Step S4 of FIG. 10 is replaced with a step where the monitor-image displaying device 34 displays, as shown in an upper portion of FIG. 28, respective ultrasonic cross-section images G1, G2, obtained by the two ultrasonic arrays A1, A2, such that respective center positions of the blood vessel 20 in the x axis are indicated or designated by respective symbols, C1, C2, and an arrow, K, representing a rotation direction about the z axis in which the z-axis rotating device 72 is rotated to zero the difference of the two center positions C1, C2. According to the symbols C1, C2 and the arrow K, displayed by the displaying device 34, an operator manually operates a manually operable input device, i.e., the keyboard 36 and/or the mouse 37 so as to control manually the z-axis rotating device 72 and thereby select a rotation angle of the ultrasonic arrays A1, A2 about the z axis. The modified form of the first embodiment enjoys the same advantages as those of the first embodiment shown in FIGS. 1 through 14.

In the second embodiment shown in FIGS. 15 through 21, the translation of the two ultrasonic arrays A1, A2 along the x axis is automatically carried out at Steps S12 and S13 of FIG. 19; and the rotation of the ultrasonic arrays A1, A2 about the z axis is automatically carried out at Steps S14 and S15 of FIG. 19. However, each of the translation and rotation of the ultrasonic arrays A1, A2 may be controlled in a manual operation.

Figure 29:
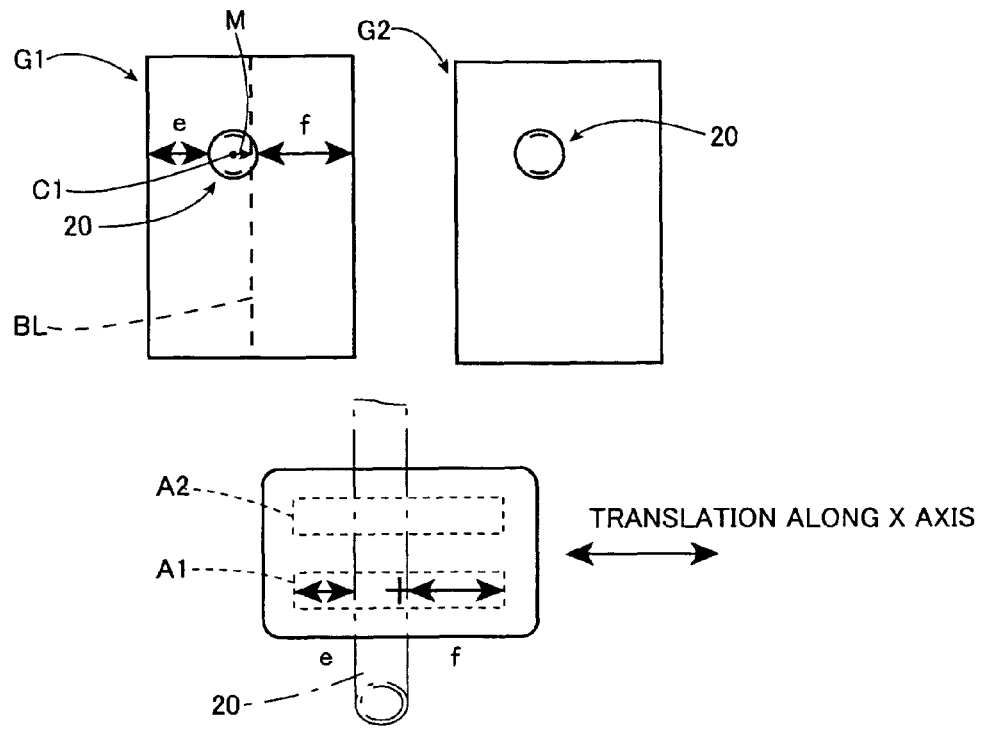
FIG. 29 is a view showing an image displayed by a displaying device employed by another blood-vessel-image measuring apparatus as a modified embodiment of the second embodiment, the displayed image being used in a manual control operation in which a center position of an ultrasonic array in a lengthwise direction thereof and a position of a blood vessel are made equal to each other by manually operating an input device, and showing an arrow indicating a movement direction along the x axis in which the x-axis moving device is operated to cause the center position of the ultrasonic array in the lengthwise direction thereof indicated by a broken line, BL, and a center position, C1, of the blood vessel in an ultrasonic image obtained by the ultrasonic array, to coincide with each other in the x-axis direction and thereby zero the difference of the two center positions.
Figure 30:
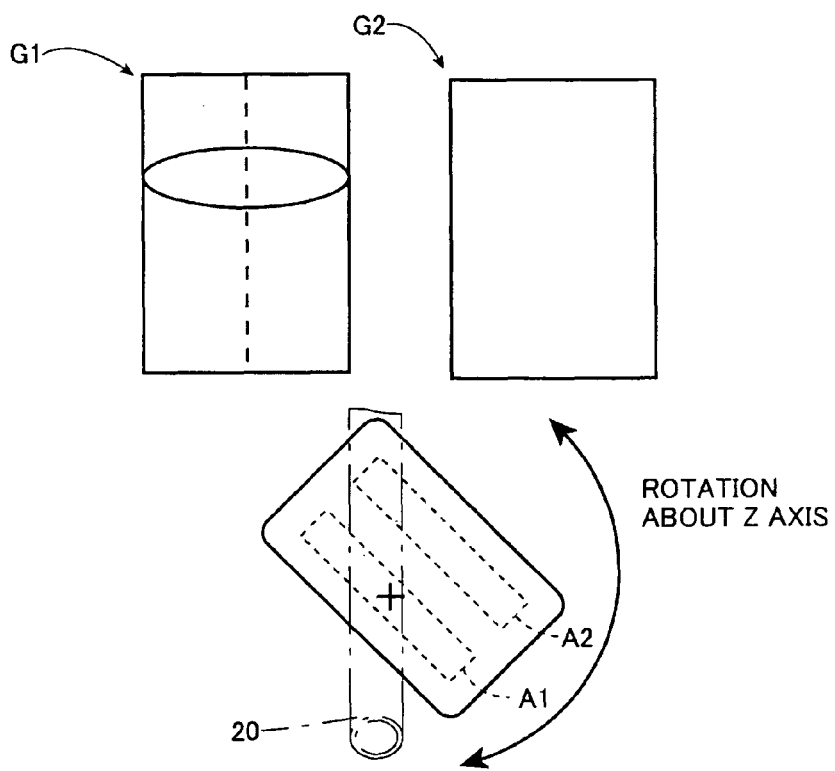
FIG. 30 is a view showing an image displayed by the displaying device employed in the modified embodiment of the second embodiment, the displayed image being used in a manual control operation in which the lengthwise direction of the ultrasonic array and a lengthwise direction of the blood vessel are caused to coincide with each other by rotating the ultrasonic array about a center position thereof as seen in the lengthwise direction thereof by manually operating the input device.

In a modified form of the second embodiment, Step S12 of FIG. 10 is replaced with a step where the monitor-image displaying device 34 displays, as shown in an upper portion of FIG. 29, respective ultrasonic cross-section images G1, G2, obtained by the two ultrasonic arrays A1, A2, such that a center position of the blood vessel 20 in the x axis is indicated by a symbols, C1, and the center position of the ultrasonic array A1 in the lengthwise direction thereof through which the z axis passes is indicated by a broken line, BL. In addition, an arrow, M, representing a movement direction, along the x axis, in which the x-axis moving device 92 is operated to zero the difference of the center position C1 and the position of the broken line BL. According to the symbol C1 and the arrow M, displayed by the displaying device 34, an operator manually operates a manually operable input device, i.e., the keyboard 36 and/or the mouse 37 so as to control manually the x-axis moving device 92 and thereby position the center position C1 of the ultrasonic array A1 at the center position BL in the x-axis direction. In addition, Step S14 of FIG. 19 is replaced with a step where the monitor-image displaying device 34 displays, as shown in an upper portion of FIG. 30, an ultrasonic cross-section image G1 that is obtained by the ultrasonic array A1 and that includes a cross-section image of the blood vessel 20. An operator manually operates a manually operable input device, i.e., the keyboard 36 and/or the mouse 37 so as to control manually the z-axis rotating device 94 and thereby select a rotation angle of the ultrasonic array A1 about the z axis, such that the ultrasonic cross-section image G1 displayed by the display device 34 becomes a longitudinal cross-section image of the blood vessel 20 that includes two parallel lines, as shown in FIG. 21. FIG. 30 shows an incomplete image of the blood vessel 20 at an intermediate time before the final, longitudinal cross-section image of the same 20, shown in FIG. 21, is obtained. The modified form of the second embodiment enjoys the same advantages as those of the second embodiment shown in FIGS. 15 through 21.

While the present invention has been described in its preferred embodiments by reference to the drawings, it is to be understood that the invention may otherwise be embodied.

For example, in the first embodiment shown in FIGS. 1 through 14, the blood-vessel-image measuring apparatus 22 employs (A) the x-axis rotating device 70 and the x-axis control means or device (Steps S2, S3) for controlling the device 70, and additionally employs (B) the z-axis rotating device 72 and the z-axis control means or device (Steps S4, S5) for controlling the device 72. However, the measuring apparatus 22 may be so modified as to employ only one of the two elements (A), (B).

In addition, in the illustrated embodiments, the respective mechanical constructions of the x-axis rotating device 70, the z-axis rotating device 72, the x-axis moving device 92, the z-axis rotating device 94, and the y-axis rotating device 110 are exemplary ones, and those may otherwise be embodied.

In addition, in the third embodiment shown in FIGS. 22 through 26, the blood-vessel-image measuring apparatus measures the short-axis images of the blood vessel 20. However, the measuring apparatus may be used to measure long-axis images of the blood vessel 20. Moreover, the second ultrasonic array A2 may be omitted.

In addition, a portion or all portions of the first embodiment shown in FIGS. 1 through 14, a portion or all portions of the second embodiment shown in FIGS. 15 through 21, and a portion or all portions of the third embodiment shown in FIGS. 22 through 26 may be employed by a common blood-vessel-image measuring apparatus. For example, the multiple-axis driving or positioning device 26 may include the x-axis rotating device 70, the z-axis rotating device 72, and the x-axis moving device 92, or may include the x-axis rotating device 70, the z-axis rotating device 72, and the y-axis rotating device 110.

In addition, in the third embodiment shown in FIG. 24, the rotation position of the two ultrasonic arrays A1, A2 about the y axis is manually changed, i.e., changed by operating the y-axis rotating device 110 under the manual control. However, the rotation position or posture of the two ultrasonic arrays A1, A2 about the y axis may be automatically changed, by a predetermined angle at each time, so as to form, between the emission surfaces S of the arrays A1, A2 and the skin surface 18 opposed to the emission surfaces S, the angle $\alpha$ assuring that the ghost images $L_1'$ caused by the multiple reflection are prevented from being produced in the respective ultrasonic images G1, G2 obtained by the arrays A1, A2. In the latter case, Steps S22 and S23 of FIG. 24 correspond to an emission-surface-angle control means or device for changing the rotation position or posture of the ultrasonic array A1 about the y axis so as to form, between the emission surface S of the array A1 and the surface of the skin 18 opposed to the emission surface S, the angle $\alpha$ assuring that the ghost image $L_1'$ caused by the multiple reflection is prevented from being produced in the cross-section image G1 obtained by the array A1. In this case, too, the emission surface S of the ultrasonic array A1 is inclined by the angle $\alpha$ relative to the surface of the skin 18 opposed to the emission surface S, so as to prevent the multiple reflection, and accordingly a highly clear and accurate transverse cross-section image of the endothelium (i.e., the inner layer $L_1$) of the blood vessel 20 is obtained.

In addition, in each of the illustrated embodiments, the keyboard 36 and/or the mouse 37 are/is used as the manually operable input device. However, the keyboard 36 and/or the mouse 37 may be replaced with a toggle switch or a joy stick.

The present invention may be embodied with various changes and improvements that may occur to a person skilled in the art, without departing from the spirit and scope of the invention.

What is claimed is:

1. A blood vessel endothelium function evaluating apparatus, comprising:
   an electronic control device for synthesizing an image based on reflected ultrasonic beams from a portion of a single blood vessel located under a skin surface and producing a transverse-cross-section image of the blood vessel to measure the transverse-cross-section image; and
   an ultrasonic probe including:
   a pair of parallel ultrasonic arrays each of which has a plurality of ultrasonic transducers arranged in one direction in an emission surface and which emits, from the emission surface, an ultrasonic beam towards the blood vessel,
   a main frame that is adapted to be placed on the skin of a living being, and
   an x-axis supporting device that is supported by the main frame and that supports the pair of ultrasonic arrays to be rotatable about an x axis parallel to the direction of arrangement of the ultrasonic transducers in the emission surface;

wherein the electronic control device includes an x-axis control device that controls a posture of the pair of ultrasonic arrays supported by the x-axis supporting device based on a distance between a first ultrasonic array and the blood vessel and a distance between a second ultrasonic array and the blood vessel such that in a y-z plane, the emission surface of the pair of ultrasonic arrays are parallel to the blood vessel, and the distance between the first ultrasonic array and the blood vessel and the distance between the second ultrasonic array and the blood vessel are equal; and wherein the electronic control device calculates a diameter of an inner layer of the blood vessel from the transverse-cross-section image of the blood vessel obtained by using the ultrasonic probe of which posture about the x-axis is controlled by the x-axis control device, and calculates a change rate of the diameter of the inner layer that represents a flow-mediated dilation following a postischemia reactive hyperemia from the diameter of the inner layer of the blood vessel.

2. The blood vessel endothelium function evaluating apparatus according to claim 1, further including:

an image displaying device which displays, in respective transverse-cross-section images obtained by the pair of ultrasonic arrays, respective positions of the blood vessel in a z-axis direction perpendicular to the respective emission surfaces of the pair of ultrasonic arrays, and an indication indicating a rotation direction about the x axis to decrease a difference of the respective positions of the blood vessel; and an input device which is manually operable in a manual operation to adjust a rotation of the pair of ultrasonic arrays, supported by the x-axis supporting device, about the x axis; and wherein the electronic control device utilizes, in the manual operation, the input device instead of the x-axis control device to adjust the emission surfaces of the pair of ultrasonic arrays to be parallel to the blood vessel.

3. The blood vessel endothelium function evaluating apparatus according to claim 1, wherein the ultrasonic probe further includes:

a z-axis supporting device that is supported by the main frame and that supports the pair of ultrasonic arrays to be rotatable about a z axis perpendicular to the emission surface;

wherein the electronic control device further includes a z-axis control device that controls a posture of the pair of ultrasonic arrays supported by the z-axis supporting device such that in the x-y plane lengthwise directions of the pair of ultrasonic arrays are perpendicular to the blood vessel; and wherein the electronic control device controls the posture of the ultrasonic probe about the z-axis by the z-axis control device, in addition to the posture control of the ultrasonic probe about the x-axis by the x-axis control device.

4. The blood vessel endothelium function evaluating apparatus according to claim 3, further including:

an image displaying device that displays, in respective transverse-cross-section images obtained by the pair of ultrasonic arrays, respective positions of the blood vessel in the x-axis direction parallel to the respective directions of arrangement of the ultrasonic transducers in the respective emission surfaces of the pair of ultrasonic arrays, and an indication indicating a rotation direction about the z axis to decrease a difference of the respective positions of the blood vessel, and an input device that is manually operable in a manual operation to adjust a rotation of the pair of ultrasonic arrays, supported by the z-axis; and wherein the electronic control device utilizes, in the manual operation, the input device instead of the x-axis control device to adjust the lengthwise directions of the pair of ultrasonic arrays to be perpendicular to the blood vessel.

5. The blood vessel endothelium function evaluating apparatus according to claim 1, wherein the ultrasonic probe further includes:

an x-axis supporting device that is supported by the main frame and that supports the pair of ultrasonic arrays to be translatable in the x-axis direction parallel to the direction of arrangement of the ultrasonic transducers in the emission surface, and a z-axis supporting device that is supported by the main frame and that supports the pair of ultrasonic arrays to be rotatable about a z axis that is perpendicular to the emission surface and that passes through the first ultrasonic array;

further including an image displaying device, which displays a longitudinal cross-section image of the blood vessel obtained by the pan of the ultrasonic arrays;

wherein the electronic control device includes a y-z-axis control device that controls the x-axis supporting device based on a distance between a first longitudinal end of the first ultrasonic array and the blood vessel and a distance between a second longitudinal end of the first ultrasonic array and the blood vessel such that the first ultrasonic array through which the z axis passes is positioned right above the blood vessel and the distance between the first longitudinal end of the first ultrasonic array and the blood vessel and the distance between the second longitudinal end of the first ultrasonic array and the blood vessel become equal, and subsequently controls the z-axis supporting device such that the direction of arrangement of the ultrasonic transducers is parallel to the blood vessel; and wherein the electronic control device creates the longitudinal-cross-section image of the blood vessel by using the ultrasonic probe of which posture in the x-axis direction and about the z-axis are controlled by the y-z-axis control device, and displays the longitudinal cross-section image of the blood vessel on the image displaying device.

6. The blood vessel endothelium function evaluating apparatus according to claim 5, wherein the image displaying device displays, in respective longitudinal-cross-section images, respective positions of the blood vessel in the x-axis direction, and an indication indicating a rotation direction about the z axis to decrease a difference of the respective positions of the blood vessel, further including an input device that is manually operable in a manual operation to adjust a movement of the pair of ultrasonic arrays, supported by the x-axis supporting device, in the x-axis direction, and a rotation of the two pair of ultrasonic arrays, supported by the z-axis supporting device, about the z axis; and wherein the electronic control device utilizes, in the manual operation, the input device instead of the x-axis control device to adjust a rotation of the pair of ultrasonic arrays such that the first ultrasonic array through which the z-axis passes is positioned right above the blood vessel and the arranging direction of the pair of ultrasonic arrays is parallel to the blood vessel.

7. The blood vessel endothelium function evaluating apparatus according to claim 1, wherein the ultrasonic probe further includes:

a y-axis supporting device that is supported by the main frame and that supports the pair of ultrasonic arrays is to be rotatable about a y axis perpendicular to the direction of arrangement of the ultrasonic transducers in the emission surface;

further including an emission-surface-angle control device that changes rotation posture of the pair of ultrasonic arrays about the y axis such that an angle to delete a ghost image produced by multiple reflection in the measured image is formed between the emission surface and an outer surface of the skin that is opposed to the emission surface; and wherein the electronic control device controls the posture of the ultrasonic probe of which posture about the y-axis by the emission-surface-angle control device, in addition to the posture control of the ultrasonic probe about the x-axis by the x-axis control device.

8. The blood vessel endothelium function evaluating apparatus according to claim 7, further including:

an image displaying device that displays an image of the blood vessel, including the endothelium, obtained by the ultrasonic array, and an input device that is manually operable in a manual operation to adjust a rotation of the pair of ultrasonic arrays supported by y-axis supporting device, about the y axis; and wherein the electronic control device changes, in the manual operation, a rotation posture of the pair of ultrasonic arrays about the y axis to form an angle for deleting a ghost image produced by multiple reflection in the measured image between the emission surface and an outer surface of the skin that is opposed to the emission instead of the emission-surface-angle control device.

* * * * *